US010400227B2

(12) United States Patent
Mahuran et al.

(10) Patent No.: US 10,400,227 B2
(45) Date of Patent: Sep. 3, 2019

(54) β-HEXOSAMINIDASE PROTEIN VARIANTS AND ASSOCIATED METHODS FOR TREATING GM2 GANGLIOSIDOSES

(71) Applicants: The University of Manitoba, Winnipeg (CA); The Hospital for Sick Children, Toronto (CA)

(72) Inventors: Don Mahuran, Toronto (CA); Brian Mark, Winnipeg (CA)

(73) Assignees: The University of Manitoba, Winnipeg, MB; The Hospital for Sick Children, Toronto, ON ( * ) Notice: Subject to any disclaimer, the term of this patent is extended or adjusted under 35 U.S.C. 154(b) by 0 days.

(21) Appl. No.: 14/660,412

(22) Filed: Mar. 17, 2015

(65) Prior Publication Data
US 2015/0258180 A1    Sep. 17, 2015

Related U.S. Application Data

(60) Provisional application No. 61/954,098, filed on Mar. 17, 2014.

(51) Int. Cl.
| | | |
|---|---|---|
| C12N 9/24 | (2006.01) | |
| A61K 38/47 | (2006.01) | |
| A61K 38/00 | (2006.01) | |

(52) U.S. Cl.
CPC ............ *C12N 9/2402* (2013.01); *A61K 38/47* (2013.01); *A61K 38/00* (2013.01); *C12Y 302/01052* (2013.01)

(58) Field of Classification Search
None
See application file for complete search history.

(56) References Cited

U.S. PATENT DOCUMENTS

| | | |
|---|---|---|
| 4,373,071 A | 2/1983 | Itakura |
| 4,401,796 A | 8/1983 | Itakura |
| 4,458,066 A | 7/1984 | Caruthers et al. |
| 4,598,049 A | 7/1986 | Zelinka et al. |
| 8,419,710 B2 | 4/2013 | Keimel et al. |
| 2005/0100986 A1* | 5/2005 | Verma ............... A61K 38/02 435/69.1 |

FOREIGN PATENT DOCUMENTS

| | | | |
|---|---|---|---|
| CA | 2888628 | | 4/2014 |
| JP | 2008206428 A | * | 9/2008 |
| WO | 2010082622 | | 7/2010 |
| WO | 2015150922 | | 10/2015 |

OTHER PUBLICATIONS

Akeboshi et al., Production of Recombinant β-Hexosaminidase A, a Potential Enzyme for Replacement Therapy for Tay-Sachs and Sandhoff Diseases, in the Methylotrophic Yeast Ogataea minuta, Appl. Environ. Microbiol., 2007, 73, 4805-12.*
Wang et al., Engineering a lysosomal enzyme with a derivative of receptor-binding domain of apoE enables delivery across the blood-brain barrier, Proc. Natl. Acad. Sci. USA, 2013, 110, 2999-3004.*
Mendel et al., Site-directed mutagenesis with an expanded genetic code, Annu. Rev. Biophys. Biol. Struct., 1995, 24, 435-62.*
English language translation of Japanese published application 2008-206428 A, 2008.*
Hepbildikler et al., Physiological Substrates for Human Lysosomal β-Hexosaminidase S, J. Biol. Chem., 2002, 277, 2562-72.*
"International Search Report and Written Opinion," for PCT Application No. PCT/IB2015/001208, dated Dec. 4, 2015 (15 pages).
Bevan, Adam K. et al., "Systemic Gene Delivery in Large Species for Targeting Spinal Cord, Brain, and Peripheral Tissues for Pediatric Disorders," Molecular Therapy, vol. 19, No. 11 (Nov. 2011), pp. 1971-1980.
Bryson, Christine J. et al., "Prediction of Immunogenicity of Therapeutic Proteins," Biodrugs, vol. 24, No. 1 (2010), pp. 1-8.
Cachon-Gonzalez, M. B. et al., "Effective Gene Therapy in an Authentic Model of Tay-Sachs-Related Diseases," Proc Natl Acad Sci (USA), vol. 103, No. 27 (Jul. 5, 2006), pp. 10373-10378.
Coloma, M. J. et al., "Transport Across the Primate Blood-Brain Barrier of a Genetically Engineered Chimeric Monoclonal Antibody to the Human Insulin Receptor," Pharmaceutical Research, vol. 17, No. 3 (2000), pp. 266-274.
Dobrenis, Kostantin et al., "Neuronal Lysosomal Enzyme Replacement Using Fragment C of Tetanus Toxin," Proc. Natl. Acad. Sic, USA, vol. 89 (Mar. 1992), pp. 2297-2301.
Duque, Sandra et al., "Intravenous Administration of Self-Complementary AAV9 Enables Transgene Delivery to Adult Motor Neurons," Molecular Therapy, vol. 17, No. 7 (Jul. 2009), pp. 1187-1196.

(Continued)

*Primary Examiner* — Robert B Mondesi
*Assistant Examiner* — Todd M Epstein
(74) *Attorney, Agent, or Firm* — Pauly, DeVries Smith & Deffner LLC

(57) ABSTRACT

Embodiments herein include variants of β-hexosaminidase that are useful for hydrolyzing GM2 ganglioside, polynucleotides encoding the same, and related methods. In various embodiments, a variant β-hexosaminidase subunit is included wherein the variant β-hexosaminidase subunit forms a homodimer under physiological conditions and wherein the variant β-hexosaminidase subunit associates with $G_{M2}$ activator protein to hydrolyze $G_{M2}$ ganglioside. In some embodiments, an isolated or recombinant polynucleotide encoding such a variant β-hexosaminidase subunit is included. In some embodiments, a method of treating a subject exhibiting an abnormal cellular accumulation of GM2 ganglioside is included wherein the method includes administering a composition including a protein variant of β-hexosaminidase or a polynucleotide encoding the same. Other embodiments are included herein.

9 Claims, 10 Drawing Sheets
(3 of 10 Drawing Sheet(s) Filed in Color)
Specification includes a Sequence Listing.

(56) References Cited

OTHER PUBLICATIONS

Federici, T. et al., "Robust Spinal Motor Neuron Transduction Following Intrathecal Delivery of AAV9 in Pigs," Gene Therapy, vol. 19 (2012), pp. 852-859.
Fernandes, Maria J. et al., "Identification of Candidate Active Site Residues inLysosomal Beta-Hexosaminidase A," The Journal of Biological Chemistry, vol. 272, No. 2 (Jan. 10, 1997), pp. 814-820.
Folch, Jordi et al., "A Simple Method for the Isolation and Purification of Total Lipides from Animal Tissues," J. Biol. Chem., vol. 226 (1957), pp. 497-509.
Gabathuler, Reinhard "Approaches to Transport Therapeutic Drugs Across the Blood-Brain Barrier to Treat Brain Diseases," Neurobiology of Disease, vol. 37 (2010), pp. 48-57.
Gray, Steven J. "Gene Therapy and Neurodevelopmental Disorders," Neuropharmacology, vol. 68 (2013), pp. 136-142.
Gray, Steven J. et al., "Preclinical Differences of Intravascular AAV9 Delivery to Neurons and Glia: A Comparative Study of Adult Mice and Nonhuman Primates," Molecular Therapy, vol. 19, No. 6 (Jun. 2011), pp. 1058-1069.
Guidotti, J. E. et al., "Adenoviral Gene Therapy of the Tay-Sachs Disease in Hexosaminidase A-Deficient Knock-Out Mice," Human Molecular Genetics, vol. 8, No. 5 (1999) pp. 831-838.
Hou, Yongmin et al., "A Pro Ser Substitution in the Beta-Subunit of Beta-Hexosaminidase A Inhibits a-Subunit Hydrolysis of GM2 Ganglioside, Resulting in Chronic Sandhoff Disease," The Journal of Biological Chemistry, vol. 273, No. 33 (Aug. 14, 1998), pp. 21386-21392.
Lacorazza, H. D. et al., "Expression of Human Beta-Hexosaminidase a-Subunit Gene (the Gene Defect of Tay-Sachs Disease) In Mouse Brains Upon Engraftment of Transduced Progenitor Cells," Nature Medicine, vol. 2, No. 4 (Apr. 1996), pp. 424-429.
Lemieux, M. J. et al., "Crystallographic Structure of Human Beta-Hexosaminidase A: Interpretation of Tay-Sachs Mutations and Loss of GM2 Ganglioside Hydrolysis," J. Mol. Biol., vol. 359 (2006) pp. 913-929.
Mahuran, Don J. "Characterization of Human Placental Beta-Hexosaminidase I2," The Journal of Biological Chemistry, vol. 265, No. 12 (Apr. 25, 1990), pp. 6794-6799.
Mahuran, Don J. et al., "The Biochemistry of HEXA and HEXB Gene Mutations Causing GM2 Gangliosidosis," Biochim Biophys Acta, vol. 1096 (1991), pp. 87-94.
Maier, Timm et al., "The X-Ray Crystal Structure of Human Beta-Hexosaminidase B Provides New Insights into Sandhoff Disease," J. Mol. Biol., vol. 328 (2003), pp. 669-681.
Mark, Brian L. et al., "Crystal Structure of Human Beta-Hexosaminidase B: Understanding the Molecular Basis of Sandhoff and Tay-Sachs Disease," J. Mol. Biol. vol. 327, (2003), pp. 1093-1109.
Martino, S. et al., "A Direct Gene Transfer Strategy via Brain Internal Capsule Reverses the Biochemical Defect in Tay-Sachs Disease," Human Molecular Genetics, vol. 14, No. 15 (2005), pp. 2113-2123.

Matsuoka, Kazuhiko et al., "Therapeutic Potential of Intracerebroventricular Replacement of Modified Hum,an Beta-Hexosaminidase B for GM2 Gangliosidosis," Molecular Therapy, vol. 19, No. 6 (Jun. 2011), pp. 1017-1024.
Mules, Emilie H. et al., "Six Novel Deleterious and Three Neutral Mutations in the Gene Encoding the a-Subunit of Hexosaminidase A in Non-Jewish Individuals," Am. J. Hem. Genet., vol. 50, (1992), pp. 834-841.
Perry, Laura C. et al., "New Approaches to Prediction of Immune Responses to Therapeutic Proteins During Preclinical Development," Drugs R D, vol. 9, No. 6 (2008) pp. 385-396.
Samaranch, Lluis et al., "AAV9-Mediated Expression of a Non-Self Protein in Nonhuman Primate Central Nervous System Triggers Widespread Neuroinflammation Driven by Antigen-Presenting Cell Transduction," Molecular Therapy, vol. 22, No. 2 (Feb. 2014), pp. 329-337.
Sharma, Rohita et al., "A Single Site in Human Beta-Hexosaminidase A Binds Both 6-Sulfate-Groups on Hexosamines and the Sialic Acid Moiety of GM2 Ganglioside," Biochim Biophys Acta, vol. 1637 (2003), pp. 113-118.
Sharma, Rohita et al., "Identification of the 6-Sulfate Binding Site Unique to a-Subunit-Containing Isozymes of Human Beta-Hexosaminidase," Biochemistry, vol. 40 (2001), pp. 5440-5446.
Sinici, Incilay et al., "In Cellulo Examination of a Beta-Alpha Hybrid Construct of Beta-Hexosaminidase A Subunits, Reported to Interact withthe GM2 Activator Protein and Hydrolyze GM2 Ganglioside," PLOS ONE, vol. 8, Issue 3 (Mar. 2013), e57908, pp. 1-8.
Smiljanic-Georgijev, Natasha et al., "Characterization of the Affinity of the GM2 Activator Protein for Flycolipids by a Fluorescence Dequenching Assay," Biochim Biophys Acta, vol. 1339 (1997) pp. 192-202.
Spencer, Brian J. et al., "Targeted Delivery of Proteins Across the Blood-Brain Barrier," Proc Natl Acad Sci USA, vol. 104, No. 18 (May 1, 2007), pp. 7594-7599.
Tropak, Michael B. et al., "A Sensitive Fluorescence-Based Assay for Monitoring GM2 Ganglioside Hydrolysis in Live Patient Cells and Their Lysates," Glycobiology, vol. 20, No. 3 (2010), pp. 356-365.
Tropak, Michael B. et al., "Pharmacological Enhancement of Beta-Hexosaminidase Activity in Fibroblasts from Adult Tay-Sachs and Sandhoff Patients," The Journal of Biological Chemistry, vol. 279, No. 14 (Apr. 2, 2004), pp. 13478-13487.
Wright, Christine S. et al., "Crystal Structure of Human GN2-Activator Protein with a Novel Beta-Cup Topology," J. Mol. Biol, vol. 304 (2000), pp. 411-422.
"International Preliminary Report on Patentability," for PCT Application No. PCT/IB2015/001208 dated Sep. 29, 2016 (11 pages).
"Extended European Search Report," for European Patent Application No. 15772341.2 dated Jul. 7, 2017 (7 pages).
"Response to Communication Pursuant to Rule 70(2) and 70a(2)," for European Patent Application No. 15772341.2 filed with the EPO Feb. 1, 2018 (18 pages).

* cited by examiner

```
HexA     SEQ ID NO: 1   1  MTSSRLWFSLLLAAAFAGRATALWPWPQNFQTSDQRYVLYPNNFQFQYDVSSAAQPGCSV    60
Variant  SEQ ID NO: 2   1  MTSSRLWFSLLLAAAFAGRATALWPWPQNFQTSDQRYVLYPNNFQFQYDVSSAAQPGCSV    60

HexA                   61  LDEAFQRYRDLLFGSGSWPRPYLTGKRHTLEKNVLVVSVVTPGCNQLPTLESVENYTLTI   120
Variant                61  LDEAFQRYRDLLFGSGSWPRPYLTGKRHTLEKNVLVVSVVTPGCNQLPTLESVENYTLTI   120

HexA                  121  NDDQCLLLSETVWGALRGLETFSQLVWKSAEGTFFINKTEIEDFPRFPHRGLLLDTSRHY   180
Variant               121  NDDQCLLLSETVWGALRGLETFSQLVWKSAEGTFFINKTEIEDFPRFPHRGLLLDTSRHY   180

HexA                  181  LPLSSILDTLDVMAYNKLNVFHWHLVDMSFPYESFTFPELMRKGSYNFVTHIYTAQDVK    240
Variant               181  LPLSSILDTLDVMAYNKLNVFHWHLVDKQSFPYESFTFPELMRKGSYS-LSHIYTAQDVK   239

HexA                  241  EVIEYARLRGIRVLAEFDTPGHTLSWGPGIPGLLTPCYSGSEPSGTFGPVNPSLNNTYEF   300
Variant               241  EVIEYARLRGIRVLAEFDTPGHTLSWGPGIPGLLTPCYSGSEPSGTFGPVNPSLNNTYEF   299

HexA                  301  MSTFFLEVSSVFPDFYLHLGGDEVDFTCWKSNPEIQDFMRKKGFGEDFKQLESFYIQTLL   360
Variant               300  MSTFFLEVSSVFPDFYLHLGGDEVDFTCWKSNPEIQDFMRKKGFGEDFKQLESFYIQTLL   359

HexA                  361  DIVSSYGKGYVVWQEVFDNKVKIQPDTIIQVWREDIPVNYMKELELVTKAGFRALLSAPW   420
Variant               360  DIVSSYGKGYVVWQEVFDNKVKIQPDTIIQVWREDIPVNYMKELELVTKAGFRALLSAPW   419

HexA                  421  YLMRISYGEDWKDYNVEPLAFEGTPEQKALVIGGEACMWGEYVDNTNLVPRLWPRAGAV   480
Variant               420  YLMRISYGQDWKLYNVEPLAFEGTPEQKALVIGGEACMWGEYVDKVDNLVPRLWPRAGAV   479

HexA                  481  AERLWSNKLTSHLTFAYERLSHFRCELIRRGVQAQPLNVFFCENDEFEQT            529
Variant               480  AERLWSNKLTRDWDDVDRLSHFRCELIRRGVNAQPLKANHNDEFEQT              528
```

FIG. 1

SEQ ID NO: 3:

atgacctcttctagactgtggttcagcctgctgctcgccgcagcctttgccggacg
ggccaccgctctttggccgtggccccagaacttccagacctctgaccagcggtacg
tgctttacccaaataacttccagtttcagtacgatgtgtccagcgccgctcagccg
ggctgttccgtgctggacgaggccttccaacgctatcgcgaccttcttttcggatc
tggctcctggccaaggccatatctcaccggaaagagacacaccttgagaagaacg
tcctcgtggtgagcgtggtgaccctggttgtaatcaactgccgaccctggaatct
gtcgagaattacactctgactattaacgacgaccaatgcctgcttctgtctgaaac
tgtctggggagcactgcggggacttgaaccttcagccagctggtgtggaagtcag
cagagggaaccttcttcatcaataagaccgaaatcgaggattttccccgcttccct
catcggggactgctgctggacactagccgccattatcttccgcttaagtccattct
ggatacoctcgacgtgatggcatacaacaaactcaatgtgttccactggcatctgg
tggacgaccagtcatttccctacgagtccttcaccttccccgaactcatgaggaag
ggaagctactctctcagccacatctacaccgcccaagacgtcaaggaagtcatcga
atatgcacgcctgcgcggaattagagtgctcgccgagttcgacaccctgggcaca
ccctgagctggggacctggcatccctggtctgctcactcctgctattcagggtca
gaaccttccggtactttggccctgtcaatcctagcctgaacaatacttacgagtt
tatgtctactttcttccttgaagtctcatcagtctttccagacttctatctgcatc
tcggaggtgatgaagtggacttcacctgttggaagtcaaaccccgaaattcaagac
tttatgcggaagaagggtttcggagaggatttcaaacaactggagagcttctacat
ccagacccttctcgacatcgtgtcctcatacgggaaggttacgtggtctggcagg
aagtgttcgacaataaggtgaagattcagcccgacaccattatccaagtctggcgg
gaggacatcccagtgaactacatgaaggaacttgagctggtgactaaggctgggtt
ccgcgctcttctcagcgctccatggtatctcaatcggatctcttacggacaggatt
ggaggaagttctacaaagtcgaaccctggctttcgaggggaccectgagcagaag
gctcttgtgatcggaggcgaggcctgcatgggggagagtacgtggatgccaccaa
cctggtgcccagactttggccaagggccggtgccgtggctgaacgcctgtggtcaa
ataagctgacccgcgatatggacgacgcctatgatagactttcacatttccggtgc
gaactggtgcggagaggggtggctgcccagccgctgtacgccgggtactgcaacca
ggagtttgagcagact

FIG. 3

α   SEQ ID NO: 1                                    [illegible]                                22
β   SEQ ID NO: 4                                    [illegible]                                42

α   --------|-----(LNPWPQNFQTSDQRYVLIPENPQFQYDVSSAQFGCSVLDEAFQKY         68
                  *   *  **        *    *   *    
β   [illegible]AKPSPRLSFLFLSVKNTPNLLHLAPENFYISHSP HRTSGPSCTLREBAFKRY    101
                  Domain I →

α   RDLLPG)[illegible](TLEKFVLVVSYVTPGCNQLFTESVENTTLTINDDQCL            126
              **      *  *   **      *      *      *         **
β   HGYIFG)[illegible](TQVCQLLVSFTLQSECDAFPRISSDESYTLLVKSPVAV           159

α   LLSETVWGALEGLSTFSQLVWKSAEGTFFINKRFIRDFPRFPHRGLLLDTSVYLPGS          185
        *   **  **   *  *    *  *  *  *   *  * *
β   LKASKVWGALRGLRTFSQLVTQDSFSTFTINRGTIRDGRSFSRKGIYIDTSKNYLDVKT        218
                                               Domain II →

α   ILDTLDVMAYNKENVFRWRLVDDGFFYESFTFPELMRKGSLPVTIFTAQDVKEVIEY          245
      *  ** *   * *    *          **
β   ILKTLDAMAFNRFTVLHMHIVDHGFFYQEIFFPELNKGSR-LSRVYTPKDVRMVIEY          277

α   ARLRGIRVLASFDTFGKTLSWGPGIRGLLTFCYS GSER SGTFGFVNPSLWRTYSFMS        302
    ******* *     *  *   *** *  * *
β   ARLRGIRVLDEFTFPGRTLSWCKGQKDLLTPCYS]KQEK(LDSFGPINPTLWRTYYSFLT       334

α   TPFLSVGSVFFDFYLELQGDEVDFTCWKSNPEIQDFMRKFGFGEGFKQLESFYIQTLLDI      362
    *** * *     *       **  *  *  ***      ***
β   TPFKRISEVFPDQFIRLGQDSVEFKCWESNPFKIQDFMRQKSFQTDFKKLESFYIQFVLDI     394

α   VSSYGKGYVVWQEVFDRKVKIQFQTIIQVWREDIPVNYMKELELVTKAGFRALLSAPWYL      422
     *    *****   *       **  *  ***** *   *    ********
β   IATINKGSIVWQSVFDDKVKLAPGTIVEVWKDS----AYPEELSRVTASGFPVILSAPWYL     451

α   [illegible]DWKDFYVEPLASEGTPEQKALVIGGEACW[illegible]LVPRLWPRASAVAS  462
           *        ***  *******
β   [illegible]DWRKYYEVEPLDFSGTQRQKLFIGGEACLW[illegible]LVLTPLWPRASAVSE  511

α   RLWSNKLTSDLTEAYERLSHFCRT[illegible]RRGVA[illegible][illegible]QSFSQT) 529
         **                     *
β   RLWSSKDVRDMDDAYDRLTRKCMFSRSTRA[illegible][illegible]CHENM)        556

FIG. 8

β-HEXOSAMINIDASE PROTEIN VARIANTS AND ASSOCIATED METHODS FOR TREATING GM2 GANGLIOSIDOSES

This application claims the benefit of U.S. Provisional Application No. 61/954,098, filed Mar. 17, 2014, the content of which is herein incorporated by reference in its entirety.

REFERENCE TO SEQUENCE LISTINGS

The present application is filed with sequence listing(s) attached hereto and incorporated by reference.

FIELD OF THE INVENTION

Embodiments herein include protein variants of β-hexosaminidase that are useful for hydrolyzing GM2 ganglioside, polynucleotides encoding the same, and related methods.

BACKGROUND OF THE INVENTION

There are two major lysosomal β-hexosaminidase (Hex) isozymes in normal human tissue: the highly stable Hex B, a homodimer of β-subunits (encoded by the HEXB gene), and the less stable Hex A, a heterodimer composed of a β and an α (encoded by the HEXA gene) subunit. These genes are evolutionarily related with the primary structures of the two subunits they encode being ~60% identical. Whereas Hex B and Hex A share many of the same natural substrates, only Hex A can hydrolyze the non-reducing terminal, β-linked, N-acetyl galactosamine residue from the acidic glycolipid GM2 ganglioside (GM2) to produce GM3 ganglioside (GM3). Because the hydrophobic GM2 normally resides in a membranous environment, Hex A is sterically hindered from efficiently binding it in vivo. This problem is overcome by the presence of a small lysosomal glycolipid transport protein, the GM2-activator protein (GM2AP). The GM2AP extracts a molecule of GM2 from the lysosomal membrane and then the complex specifically binds to soluble Hex A, forming the active quaternary structure.

A deficiency of either of the two Hex A subunits or the GM2AP, due to a mutation in their respective genes, can lead to the accumulation of GM2 in the lysosomes of primarily neuronal cells, where the synthesis of the more complex gangliosides is the highest. This accumulation leads to neuronal cell death and one of three similar neurodegenerative diseases collectively known as GM2 gangliosidosis. These diseases include Tay-Sachs disease (TSD, MIM #272800), α-subunit deficiencies, Sandhoff disease (SD, MIM #268800), α-subunit deficiencies, and deficiencies in the GM2AP which result in the rare AB-variant form (MIM #272750).

SUMMARY OF THE INVENTION

In one aspect of the disclosure, a novel variant α-hexosaminidase protein is included that, acting as a homodimer, can hydrolyze GM2 ganglioside (GM2) in the presence of human GM2AP. Homodimers described herein are able to efficiently bind and hydrolyze GM2 in cellulo.

In an embodiment, a variant α-hexosaminidase subunit is included wherein the variant α-hexosaminidase subunit forms a stable homodimer under physiological conditions and wherein the variant α-hexosaminidase subunit associates with $G_{M2}$ activator protein to hydrolyze $G_{M2}$ ganglioside. The variant can comprise an amino acid sequence having at least 80% sequence identity to residues 89-529 of SEQ ID NO: 1, conservative variants thereof, or alpha/beta alignment variants thereof.

In one embodiment the variant hexosaminidase α-subunit comprises one or more of the substitutions and/or deletions listed in Table 4. In one embodiment, the variant comprises one or more substitutions at a position selected from S184, P209, N228, V230, T231, P429, K432, D433, I436 or V436, N466, S491, L493, T494, F495, E498, L508, Q513, N518, V519, F521 and E523 corresponding to the amino acid numbering set forth in SEQ ID NO: 1. In one embodiment, the variant comprises one or more substitutions selected from S184K, P209Q, N228S, V230L, T231S, P429Q, K432R, D433K, I436K or V436K, N466A, S491R, L493M, T494D, F495D, E498D, L508V, Q513A, N518Y, V519A, F521Y and E523N corresponding to the amino acid numbering set forth in SEQ ID NO: 1. In one embodiment, the variant comprises between 5-10, 10-15, 15-20 or 21 substitutions selected from S184K, P209Q, N228S, V230L, T231S, P429Q, K432R, D433K, I436K or V436K, N466A, S491R, L493M, T494D, F495D, E498D, L508V, Q513A, N518Y, V519A, F521 Y and E523N. In one embodiment, the variant comprises a deletion at position P229 corresponding to the amino acid numbering set forth in SEQ ID NO: 1.

In one embodiment, the variant hexosaminidase α-subunit comprises, consists essentially of, or consists of an amino acid sequence with at least 70%, at least 80%, at least 90%, or at least 95% sequence identity to SEQ ID NO: 1 or to mature forms of the polypeptide set forth in SEQ ID NO: 1. In one embodiment, the variant hexosaminidase α-subunit comprises, consists essentially of or consists of an amino acid sequence with at least 70%, at least 80%, at least 90%, or at least 95% sequence identity to SEQ ID NO: 2 or to mature forms of the polypeptide set forth in SEQ ID NO: 2. In one embodiment, the variant comprises, consists essentially of, or consists of the amino acid sequence set forth in SEQ ID NO: 2, or to mature forms thereof.

In one embodiment, the variant hexosaminidase α-subunit described herein comprises mature forms of the polypeptide. For example, in one embodiment, the variant α-subunit does not contain an N-terminal signal peptide, such as amino acids 1 to 22 set forth in SEQ ID NO: 1 or amino acids 1 to 22 set forth in SEQ ID NO: 2. In one embodiment, the variant α-subunit does not contain the loop region set forth in amino acids 75 to 88 of SEQ ID NO: 1 or SEQ ID NO: 2. In one embodiment, the variant hexosaminidase α-subunit comprises, consists essentially of, or consists of an amino acid sequence with at least 70%, at least 80%, at least 90%, or at least 95% sequence identity to a mature form of the amino acid set forth in SEQ ID NO: 2.

In one embodiment, the variant hexosaminidase α-subunit is glycosylated. In one embodiment, the variant hexosaminidase α-subunit comprises one or more mannose-6-phosphate molecules. Optionally, the mannose-6-phosphate molecules are attached to Asn-linked oligosaccharide(s) present in the variant hexosaminidase α-subunit.

In one embodiment, the variant hexosaminidase α-subunit forms a protein complex with another variant hexosaminidase α-subunit as described herein, forming an active dimer such as a homodimer.

In one aspect of the disclosure, there is also provided a protein complex comprising one or more variant hexosaminidase α-subunits as described herein. In one embodiment, the protein complex is a dimer. In one embodiment, the protein complex is a homodimer comprising two variant hexosaminidase α-subunits as described herein. In one embodiment, the protein complex comprises two variant hexosaminidase α-subunits as set forth in SEQ ID NO: 2, or mature forms thereof.

In one embodiment, the protein complex has increased stability relative to Hexosaminidase A. For example, in one embodiment the protein complex has increased resistance to heat denaturation in vitro relative to Hexosaminidase A. In one embodiment, the protein complex has both MUG (4-methylumbelliferyl-2-acetamido-2-deoxy-β-D-glucopyranoside) and MUGS (4-methylmbeliferyl-2-acetamido-2-deoxy-β-D-glucopyranoside-6-sulfate) hydrolysis activity. In one embodiment, the protein complex has a decreased MUG/MUGS hydrolysis ratio relative to Hexosaminidase A. For example, in one embodiment, the protein complex has an increased specific activity (measured as nmole MUGS/hr/mg of protein) relative to Hexosaminidase A.

In one embodiment, the protein complex has GM2 ganglioside hydrolysis activity. In one embodiment, the protein complex has GM2 ganglioside hydrolysis activity in cellulo. For example, in one embodiment the protein complex has GM2 ganglioside hydrolysis activity in brain cells such as glial cells or neuronal cells, or peripheral neuronal cells. In one embodiment, the protein complex is transported to lysosomes. In one embodiment, the protein complex has GM2 ganglioside hydrolysis activity in the presence of GM2AP. In a preferred embodiment, the protein complex is a homodimer.

In one embodiment, the variant hexosaminidase α-subunit as described herein is conjugated to a cell-penetrating peptide or a molecule that targets membrane receptors undergoing endocytosis. In one embodiment, a nucleic acid molecule encoding for a variant hexosaminidase α-subunit as described herein is conjugated to a cell-penetrating peptide or a molecule that targets membrane receptors undergoing endocytosis. In one embodiment, a variant hexosaminidase α-subunit or nucleic acid encoding for a variant hexosaminidase α-subunit is conjugated to a peptide or other molecule that facilitates crossing the blood brain barrier.

In another aspect of the disclosure, there is provided a nucleic acid molecule encoding for a variant hexosaminidase α-subunit as described herein. For example, in one embodiment the nucleic acid molecule encodes for a variant hexosaminidase α-subunit with one or more of the substitutions and/or deletions at the positions listed in Table 4. In one embodiment, the nucleic acid molecule encodes for a variant hexosaminidase α-subunit comprising between 5-10, 10-15, 15-20 or 21 of the substitutions listed in Table 4. In one embodiment, the nucleic acid molecule encodes for a variant hexosaminidase α-subunit comprising a deletion at position P229 corresponding to the amino acid numbering set forth in SEQ ID NO: 1. In one embodiment, the nucleic acid molecule encodes for a variant hexosaminidase α-subunit comprising a deletion at position P229 and between 5-10, 10-15, 15-20 or 21 substitutions selected from S184K, P209Q, N228S, V230L, T231S, P429Q, K432R, D433K, I436K or V436K, N466A, S491R, L493M, T494D, F495D, E498D, L508V, Q513A, N518Y, V519A, F521Y and E523N corresponding to the amino acid numbering set forth in SEQ ID NO: 1. In one embodiment, the nucleic acid molecule encodes for a protein that comprises, consists essentially of, or consists of an amino acid sequence with at least 70%, at least 80%, at least 90%, or at least 95% sequence identity to the variant hexosaminidase α-subunit set forth in SEQ ID NO: 2, or to mature forms of SEQ ID NO: 2. In one embodiment, the nucleic acid molecule comprises, consists essentially of, or consists of a nucleic acid sequence with at least 70%, at least 80%, at least 90% or at least 95% sequence identity to the nucleic acid sequence set forth in SEQ ID NO: 3. In one embodiment, the nucleic acid molecule comprises, consists essentially of, or consists of the nucleic acid sequence set forth in SEQ ID NO: 3. In one embodiment, the nucleic acid molecule is DNA or RNA. Optionally, the nucleic acid molecule is a cDNA molecule. In one embodiment, the sequence of the nucleic acid molecule is codon-optimized for expression in a particular host cell, such as a mammalian host cell.

In another aspect, there is provided a vector comprising a nucleic acid molecule encoding a variant hexosaminidase α-subunit as described herein. In one embodiment, the vector comprises a nucleic acid sequence with at least 70%, at least 80%, at least 90% or at least 95% sequence identity to the nucleic acid sequence set forth in SEQ ID NO: 3. In one embodiment, the vector is suitable for use in gene therapy for the treatment of GM2 gangliosidosis. In one embodiment, the vector is a retroviral vector. In one embodiment, the vector is an adeno-associated viral (AAV) vector. In one embodiment, the vector is a RNA vector such as a lentivirus vector. In one embodiment, the nucleic acid sequence is operatively linked to a promoter. Also provided is a host cell transfected with a nucleic acid molecule or vector encoding a variant hexosaminidase α-subunit as described herein. In one embodiment, the host cell is a mammalian host cell.

In one aspect, there is provided a method of producing a variant a variant hexosaminidase α-subunit as described herein. In one embodiment, the method comprises culturing a host cell transfected with a vector encoding a variant hexosaminidase α-subunit under conditions suitable for the expression of the variant hexosaminidase α-subunit. Optionally, the method comprises isolating the variant hexosaminidase α-subunit or a protein complex comprising the variant hexosaminidase α-subunit from the host cell. In one embodiment, the variant hexosaminidase α-subunit is glycosylated by the host cell. In one embodiment, the host cell produces mature forms of the variant hexosaminidase α-subunit.

In another aspect, there is provided a method for hydrolyzing GM2 ganglioside in a cell. In one embodiment, the method comprises contacting the cell with a variant hexosaminidase α-subunit or protein complex comprising a variant hexosaminidase α-subunit as described herein. In another embodiment, the method comprises transfecting the cell with a nucleic acid molecule encoding a variant hexosaminidase α-subunit as described herein. In one embodiment, the cell is in vitro, in vivo or ex vivo. In one embodiment, the cell is a brain cell such as a glial cell or neuronal cell or a peripheral neuronal cell. In one embodiment, the cell has a lysosomal accumulation of GM2. In one embodiment, the cell has a mutation associated with GM2 gangliosidosis, optionally Tay-Sachs disease or Sandhoff disease.

In another aspect there is provided a method for treating GM2 gangliosidosis in a subject in need thereof. In one embodiment, the method comprises comprising administering to the subject a variant hexosaminidase α-subunit or protein complex comprising a variant hexosaminidase α-subunit as described herein, such as for enzyme replacement therapy. In one embodiment, the method comprises administering to the subject a nucleic acid molecule or vector encoding a variant hexosaminidase α-subunit as described herein, such as for gene therapy. For example, in one embodiment the method comprises transfecting one or more cells in the subject with a nucleic acid molecule or vector encoding a variant hexosaminidase α-subunit as described herein. In one embodiment, the subject has Tay-Sachs disease or Sandhoff disease. In one embodiment, the subject is a human.

Also provided is the use of a variant hexosaminidase α-subunit, a nucleic acid encoding a variant hexosaminidase α-subunit, a cell transfected with a nucleic acid encoding a variant hexosaminidase α-subunit or a protein complex comprising a variant hexosaminidase α-subunit as described herein for the treatment of GM2 gangliosidosis in a subject in need thereof. Also provided is a variant hexosaminidase α-subunit, a nucleic acid encoding a variant hexosaminidase α-subunit, a cell transfected with a nucleic acid encoding a variant hexosaminidase α-subunit or a protein complex comprising a variant hexosaminidase α-subunit as described herein for use in the treatment of GM2 gangliosidosis or for the manufacture of a medicament for the treatment of GM2 gangliosidosis. In one embodiment, the subject has Tay-Sachs disease or Sandhoff disease.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will be described in relation to the drawings in which:

FIG. 1 shows the changes made to the primary structure of the α-subunit of Hex A (SEQ ID NO: 1) and the resulting variant hexosaminidase α-subunit (SEQ ID NO: 2). Exchanges; i.e., from those in the wild-type α to those present in the wild-type β-subunit; of the boxed residues at positions S184K, P209Q, N228S, delete (Δ)P229, V230L, T231S, N466A, L508V, Q513A, N518Y, V519A, F521Y and E523N, using the position numbering of SEQ ID NO: 1, are believed to be involved in forming the β-like dimer interface, and exchanges of the boxed residues at positions K432R, D433K, I436K (or V436K), S491R, L493M, T494D, F495D and E498D, are believed to be part of the β-domain allowing Hex A to interact with the GM2 activator protein. The exchange of residues at position 429, i.e. P429Q, is believed to be involved in both aspects of the β-subunit's unique functions.

FIG. 2 shows a model of the active quaternary complex composed of Hex A (α-subunit and β-subunit) along with the GM2 activator protein (GM2AP) with a molecule of GM2-ganglioside inserted into the α-subunit active site. The α-subunit is drawn in black on the left (cartoon format); whereas, the β-subunit is drawn in light grey on the right (cartoon format). GM2AP is drawn in a wireframe (thin ribbon) format to distinguish it from the α- and β-subunits and atoms of the GM2 ganglioside are shown as spheres to distinguish it from protein. The patch on the β-subunit predicted to bind GM2A is shown as a light grey surface and residues comprising the analogous region on the α-subunit are also shown as a black surface. Residues forming the black patch on the α-subunit were mutated to match those of the β-subunit in the variant α-subunit such that when the variant α-subunits form a homodimer, there will be a GM2AP binding patch on both subunits, one of which will adopt the position shown for the light grey surface of the β-subunit. The residues involved in the dimer interface are shown as sticks.

FIG. 3 shows the codon optimized nucleotide sequence of the variant hexosaminidase α-subunit (SEQ ID NO: 3).

FIG. 4 shows the HPTLC separation of the Folch-extracted NBD-glycolipids resulting from in cellulo fluorescent NBD-GM2 (2-nitro1,3-benzoxadiazol (NBD)-4-yl, covalently attached to a short (C6) sn2 acyl chain of lyso-GM2 ganglioside) assays of three single colonies, T1, T2 & T3 (3 individual experiments), of TSD Glial cells permanently expressing the variant α-subunit (UT1-UT3=untransfected TSD Glial cells, Std=NBD-lipid standards.

FIG. 5 shows a Western blot using a rabbit IgG against human Hex A. Wt F (wild type human fibroblasts); Ut G (untransfected Glial cells); 150 mM (150 mM NaCl step elution from the DEAE (diethylaminoethyl) column (variant α-subunit-β heterodimer & variant α-subunit precursor; likely some mature variant α-subunit homodimer also elutes with the NaCl concentration step)); 500 mM (500 mM NaCl step elution from the DEAE column (mature variant α-subunit homodimer)). Variant P refers to the precursor and Variant M refers to the mature form. The MUG to MUGS ratios are also shown at the bottom.

FIG. 6 shows the over-night in vitro NBD-GM2 hydrolysis assay of the isolated variant α-subunit homodimer with purified Hex A as positive control and purified Hex B used as negative control. The samples of Hex A, the variant α-subunit homodimer and Hex B had the same number of MUG units (150 nmol/hr), Ctrl has no enzyme source and LD contains the NBD-lipid standards.

FIG. 7 shows that when untransfected TSD skin fibroblast cells (control) are grown in media in which transfected TSD Glial cells, expressing the hybrid, had been grown for 48 hr (conditioned media (C-Media)) a ~38 fold increase in intracellular MUGS activity is obtained. If the same cells are grown in conditioned media containing 5 mM mannose-6-phosphate, only an ~10-fold increase is obtained (C-Media & M6P). These data confirm that mannose-6-phosphate is present on the variant's Asn-linked oligosaccharides and that the secreted variant enzyme can interact with the mannose-6-phosphate receptor located on the plasma membrane of other non-transfected cells.

FIG. 8 shows a pair-wise sequence alignment and secondary structure of the native human hexosaminidase α-subunit versus the native human hexosaminidase β-subunit.

FIG. 9 shows an electrostatic potential surface map and dimer interface of human Hex B.

FIG. 10 shows the predicted model of human Hex A-GM2-activator quaternary complex.

DETAILED DESCRIPTION OF THE INVENTION

The inventors have developed novel variant β-hexosaminidase proteins (and polynucleotides coding for the same) that, acting as a homodimer, can hydrolyze GM2 ganglioside (GM2) in the presence of human GM2AP. The variant β-hexosaminidase protein homodimers described herein are able to efficiently bind and hydrolyze GM2 in cellulo. As one example (as set out in Example 1 below), the inventors substituted into the cDNA for hexosaminidase subunit a nucleotides that encode 21 aligned residues uniquely found in the β-subunit, while deleting one codon for an α-subunit residue not encoded in the β-subunit. Each of these substitutions and the deletion are identified in Table 4. These amino acid residues were then predicted by the inventors to be involved in either the formation of the subunit-subunit interface (to convey β-subunit-like stability to the homodimer) or the active quaternary complex (Hex A bound to the GM2-GM2AP complex) as shown in FIG. 2. Remarkably, the resulting variant protein was shown to form a stable homodimer, similar to Hex B, and be efficiently transported via the manose-6-phosphate receptor to the lysosome where it was able to hydrolyze GM2 using GM2AP as a substrate-specific co-factor. Similar to endogenous Hex A, post-translational modifications of the variant result in the addition of mannose-6-phosphate molecules to the Asn-linked oligosaccharides(s) present in the variant subunits. These modified oligosaccharides are then recognized and bound by mannose-6-phosphate receptors in the endoplasmic reticulum/Golgi, facilitating the transportation of the protein to the lysosome. Furthermore, fibroblast cells from a Sandhoff patient, deficient in β-hexosaminidase A and B, grown in medium containing the variant protein described herein can internalize the protein via mannose-6-phosphase receptors on their plasma membrane, resulting in the transport of the variant protein to the lysosome.

Definitions

Figure 2:

As used herein, the term "variant" refers to a polypeptide that comprises one or more differences in the amino acid sequence of the variant relative to a natural occurring reference sequence. For example, a "variant" polypeptide may include one or more deletions, additions or substitutions relative to a reference sequence. In one embodiment, the reference sequence codes for a naturally occurring hexosaminidase α-subunit, optionally the hexosaminidase α-subunit set forth in SEQ ID NO: 1. In one embodiment, the variant comprises one or more of the amino acid changes identified in Table 4. The term "variant" is not intended to limit the variant polypeptide to only those polypeptides made by the modification of an existing polypeptide or nucleic acid molecule encoding the reference sequence, but may include variant polypeptides that are made de novo or starting from a polypeptide other than the reference sequence. In one embodiment, the variant hexosaminidase α-subunits described herein form a homodimer. In one embodiment, the variant hexosaminidase α-subunits described herein are capable of hydrolyzing GM2 ganglioside.

As used herein "hexosaminidase α-subunit" refers to a naturally occurring polypeptide encoded by the HEXA gene, including but not limited to the gene defined by NCBI Reference Sequence Accession number NM 000520. In one embodiment, the hexosaminidase α-subunit has the amino acid sequence set forth in SEQ ID NO: 1. In a preferred embodiment, "hexosaminidase α-subunit" refers to a naturally occurring polypeptide encoded by a HEXA gene that, when formed into an active homodimer as measured by MUG (4-methylumbelliferyl-2-acetamido-2-deoxy-β-D-glucopyranoside) or MUGS (4-methylumbelliferyl-2-acetamido-2-deoxy-β-D-glucopyranoside-6-sulfate), do not hydrolyze GM2 ganglioside in a human GM2AP-dependent manner.

As used herein "protein complex" refers to a group of two or more associated polypeptides that interact through non-covalent protein-protein interactions. Examples of a protein complex include protein dimers. In one embodiment, the protein complex is a homodimer that comprises two subunits that are largely identical and share the same amino acid sequence. In one embodiment, the protein complex comprises two variant hexosaminidase α-subunits as described herein, such as two variant hexosaminidase α-subunits as set forth in SEQ ID NO: 2.

As used herein "GM2 ganglioside" refers to the ganglioside sometimes known as β-D-GalNAc-(1→4)-[α-Neu5Ac-(2→3)]-β-D-Gal-(1→4)-β-D-Glc-(1⇔1)-N-octadecanoyl-sphingosine that is associated with Tay-Sachs disease and is typically hydrolysed to GM3 ganglioside in the lysosomes of healthy subjects.

As used herein, "GM2 ganglisidosis" refers to a condition characterized by the accumulation of GM2 ganglioside in the lysosomes that eventually lead to neuronal cell death. Examples of GM2 gangliosidoses include Tay-Sachs disease or Sandhoff disease. In one embodiment, GM2 gangliosidosis refers to a condition characterized by a β-hexosaminidase A (Hex A) deficiency. In one embodiment, "GM2 gangliosidoses" result from a deficiency of either the α- or β-subunit in the enzyme β-hexosaminidase A.

As used herein, the term "alpha/beta alignment variant" shall refer to sequences wherein substitutions and or deletions are made which correspond to the variation found in particular amino acid residues at an equivalent position when comparing native hexosaminidase α-subunit sequences to native hexosaminidase β-subunit sequences. By way of example, in the native sequence for hexosaminidase α-subunit there is a glycine residue at position 367 and in the native sequence for hexosaminidase β-subunit there is an asparagine residue at position 399 (which corresponds to the same position when the sequences are aligned). An alpha/beta alignment variant can therefore include either glycine or asparagine at this position, unless a different mutation has specifically been required to the contrary.

As used herein, the term "stable homodimer" with reference to homodimers of variant β-hexosaminidase subunits herein shall refer to homodimers exhibiting increased stability relative to Hexosaminidase S As used herein, the term "conservative variant" shall refer to sequences which reflect the incorporation of conservative amino acid substitutions. Conservative substitution tables are well known in the art (see for example Creighton (1984) Proteins. W. H. Freeman and Company (Eds) and Table 1 below),

TABLE 1

Examples of Conservative Amino Acid Substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Products and Compositions

In one aspect, the present description provides variant hexosaminidase α-subunits and associated products, methods and uses. In one embodiment, the variants are distinguished from endogenous hexosaminidase α-subunits in that they are able to form a stable protein complex comprising a homodimer, which can then interact with the human GM2AP to hydrolyze GM2 ganglioside in vivo. In one embodiment, the variant hexosaminidase α-subunits described herein form a homodimer more stable than HexS, which is a homodimer of non-variant (natural occurring) hexosaminidase α-subunits. In one embodiment, the variants have sequence identity to the hexosaminidase α-subunit (SEQ ID NO: 1) shown in FIG. 1, or to the mature form thereof. In one embodiment, the variants are distinguished from endogenous hexosaminidase α-subunits in that they comprise one or more of the amino acid changes at positions corresponding to those listed in Table 4.

In one embodiment, the variant hexosaminidase α-subunit comprises one or more substitutions and/or deletions selected from those positions listed in Table 4. In one embodiment, the variant comprises one or more exchanges, i.e. α-subunit sequence replace by the aligned sequence in the β-subunit, at positions in the α-subunit selected from S184, P209, N228, V230, T231, P429, K432, D433, I436, N466, S491, L493, T494, F495, E498, L508, Q513, N518, V519, F521 and E523 corresponding to the amino acid numbering set forth in SEQ ID NO: 1. For example, in one embodiment, the variant comprises one or more substitutions selected from S184K, P209Q, N228S, V230L, T231S, P429Q, K432R, D433K, I436K, N466A, S491R, L493M, T494D, F495D, E498D, L508V, Q513A, N518Y, V519A, F521Y and E523N corresponding to the amino acid numbering set forth in SEQ ID NO: 1, and optionally a deletion at position P229 corresponding to the amino acid numbering set forth in SEQ ID NO: 1. While the substitutions and deletion listed in Table 4 have been defined by reference to the endogenous or wild-type hexosaminidase α-subunit (SEQ ID NO: 1), a skilled person would readily be able to determine which residues correspond to those listed in Table 4 in a different hexosaminidase α-subunit sequence in order to introduce the substitutions and/or deletion into said different hexosaminidase α-subunit to produce a variant. For example, a skilled person would be able to perform an alignment between a hexosaminidase α-subunit sequence that differs from SEQ ID NO: 1 (such as a hexosaminidase α-subunit sequence with one or more naturally occurring mutations or a sequence from a non-human species) and SEQ ID NO: 1 in order to determine which residues correspond to the positions listed in Table 4.

In one embodiment, the variant comprises between 5-10, 10-15, 15-20 or 21 substitutions selected from S184K, P209Q, N228S, V230L, T231S, P429Q, K432R, D433K, I436K or V436K, N466A, S491R, L493M, T494D, F495D, E498D, L508V, Q513A, N518Y, V519A, F521Y and E523N corresponding to the amino acid numbering set forth in SEQ ID NO: 1. In one embodiment, the variant comprises a deletion at position P229 corresponding to the amino acid numbering set forth in SEQ ID NO: 1. In one embodiment, the variant comprises 2, 3, 4, 5, 6, 7, 8, 9, 10, 11, 12, 13, 14, 15, 16, 17, 18, 19, 20 or 21 of the substitutions listed in Table 4, and optionally a deletion at position P229. A skilled person would be able to identify variants that comprise one or more of the amino acid changes listed in Table 4 and, for example, have the functional properties of forming a homodimer and/or GM2 ganglioside hydrolysis such as by following the experimental protocols identified in Example 1.

In one embodiment, the variant hexosaminidase α-subunit described herein, or a protein complex thereof, is conjugated to a molecule that facilitates entry of the protein into the cell such as a cell penetrating peptide or a molecule that targets membrane receptors undergoing endocytosis. For example, in one embodiment, the cell penetrating peptide is selected from TAT, Angiopep, penetratin, TP, rabies virus glycoprotein (RVG), prion peptide, and SynB. In one embodiment, the variant is conjugated to the atoxic fragment C of tetanus toxin (TTC). Alternatively or in addition, the variant hexosaminidase α-subunit or a protein complex thereof may be conjugated to a peptide or other molecule that facilitates crossing the blood brain barrier. Various conjugates useful for facilitating crossing the blood brain barrier are known in the art, including but not limited to those described in Reinhard Gabathuler, Neurobiology of Disease 37 (2010) 48-57; Spencer B J, and Verma I M, Proc Natl Acad Sci USA. 2007 May 1; 104(18):7594-930; Coloma et al., Pharm Res. 2000 March; 17(3):266-74; and Dobrenis et al, Proc. Natl. Acad. Sci. USA Vol. 89, pp. 2297-2301, March 1992. In one embodiment, the variant hexosaminidase α-subunit or protein complex is conjugated to the lipoprotein receptor-binding domain of apolipoprotein-B (ApoB-BD). In one embodiment, the variant hexosaminidase α-subunit or protein complex thereof is conjugated to a peptide binding domain associated with the transferrin receptor or insulin-like growth factor receptor.

Figure 4:
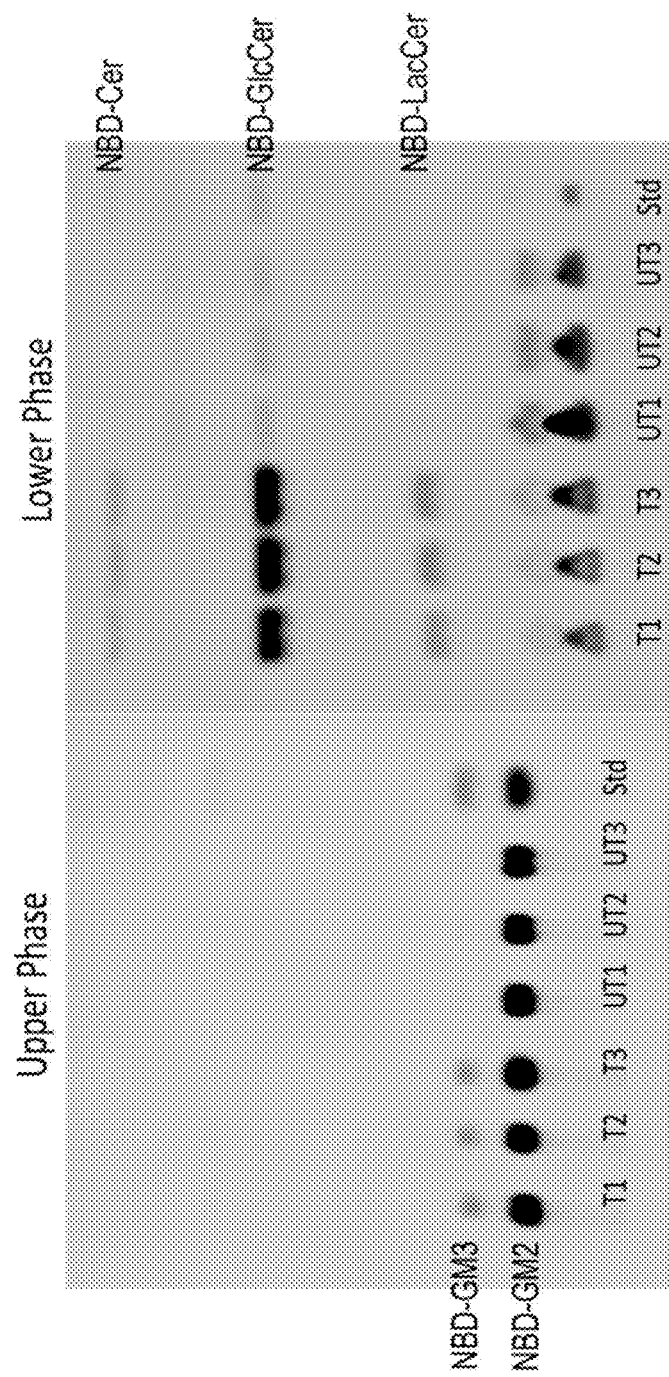

In one embodiment, the variant hexosaminidase α-subunits described herein have sequence identity to the hexosaminidase α-subunit set forth in SEQ ID NO: 1, to the exemplary variant hexosaminidase α-subunit set forth in SEQ ID NO: 2, or to mature forms thereof. In an embodiment, the variant hexosaminidase α-subunit comprises a sequence that comprises, consists essentially of, or consists of an amino acid sequence with at least: 30%, 40%, 50%, 60%, 70%, 80%, 85%, 90% or 95% sequence identity to SEQ ID NO: 1 or to SEQ ID NO: 2. In one embodiment, the variant hexosaminidase α-subunit comprises, consists essentially of, or consists of the amino acid sequence set forth in SEQ ID NO: 2. In one embodiment, the variant hexosaminidase α-subunit comprises, consists essentially of, or consists of the mature form of the amino acid sequence set forth in SEQ ID NO: 2. An exemplary mature form of the hexosaminidase β-subunit is shown in FIG. 4 of Mark et al., "Crystal Structure of Human β-Hexosaminidase B: Understanding the Molecular Basis of Sandhoff and Tay-Sachs Disease", Journal of Molecular Biology Volume 327, Issue 5, 11 Apr. 2003, Pages 1093-1109, which is hereby incorporated by reference in its entirety.

The crystal structure of Hex B, Hex A and the GM2AP have been elucidated and a model for the active quaternary structure, i.e. Hex A-GM2AP-GM2 complex, generated. Although each subunit has an active site, residues from the neighboring subunit in the dimer are needed to stabilize and complete it. Thus monomeric subunits are not active. Furthermore, the structures confirm previous findings that the ability of the α-active site to efficiently hydrolyze negatively charged substrates, e.g. MUGS and GM2, comes primarily from two aligned amino acid differences in the subunits, i.e. α-N424R and β-D453L. The basic R424 residue in the α-subunit can ion pair with either the 6-sulfate of MUGS or the sialic acid of GM2, whereas the acidic D452 residue in the β subunit repels these same moieties. Finally several unique areas in both the α- and β-subunits were identified as being potentially important in facilitating the formation of the active quaternary structure with the GM2A protein.

Figure 9:
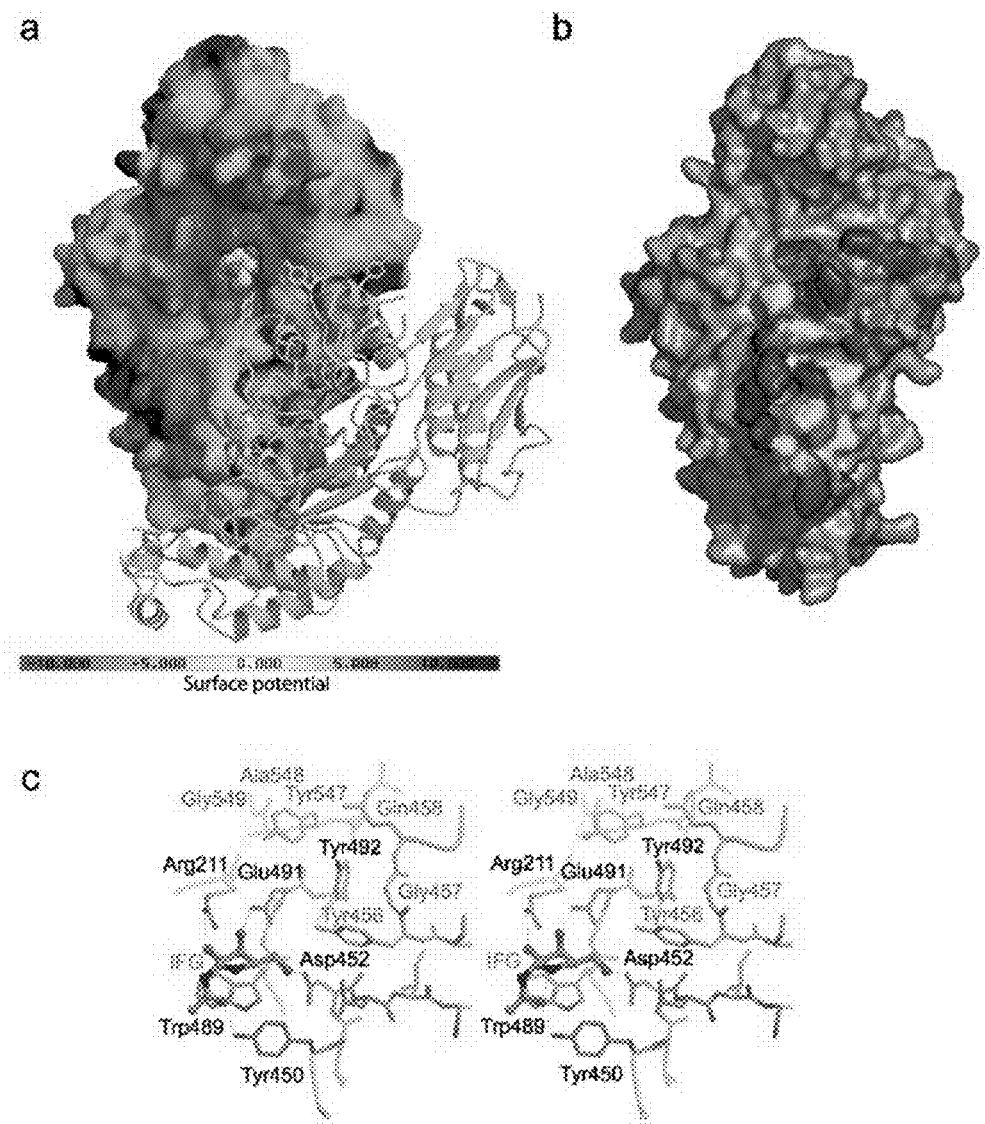

An electrostatic potential surface map and dimer interface of human Hex B was generated and is shown in FIG. 9 (a-c). FIG. 9 (a) shows a solvent-accessible surface, drawn over one b-subunit and colored with regions of positive charge in blue and negative charge in red, reveals an overall negative charge about the active site. The other subunit of the homodimer is represented by a ribbon diagram with domain I in green and the catalytic (b/a)8 domain II in yellow. The intermediate analogue NAG-thiazoline, bound in the active site of each subunit is shown as a space-filling model with carbon atoms in gray, oxygen in magenta, nitrogen in blue and sulfur in yellow. FIG. 9 (b) shows a surface rendering of a single b-subunit showing the extensive surface area buried at the dimer interface as determined using the CNS program.74 Polar side-chains are colored blue, hydrophobic side-chains in yellow, backbone atoms in forest green, charged residues in magenta and residues not involved in dimerization are colored gray. The active site pocket is colored red ((b) was drawn using the program PyMOL85). FIG. 9 (c) shows active site residues (gray) stabilized by interactions from residues of the partnering subunit (yellow). The 2-fold symmetry at the dimer interface results in both active sites experiencing the same stabilizing effects from the associated monomer. The crystallographically determined position of GalNAc-isofagomine (IFG) in the active site of each subunit demonstrates that four of the six hydrogen bonds between the enzyme and inhibitor depend on stabilizing interactions from the partnering subunit. In the absence of the protein-protein interactions that are formed upon dimerization, Arg211, Glu491, Asp452 and Tyr450 are most likely too unstructured to be catalytically active.

Figure 10:
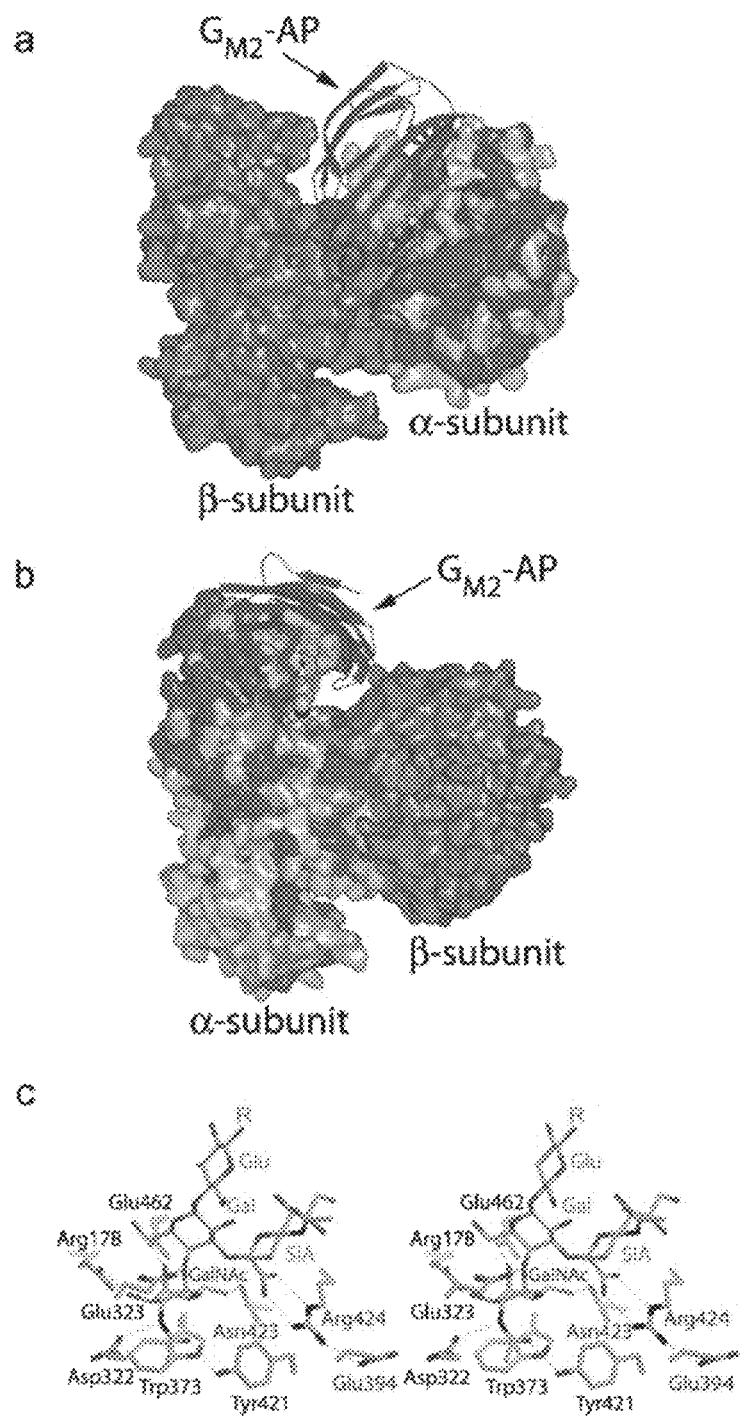

FIG. 10 shows the predicted model of human Hex A-GM2-activator quaternary complex. (a and b) Two views of the predicted quaternary complex. Residues of the α-subunit identical to those of the b-subunit are colored blue, non-identical residues are colored light brown. Most of the conserved amino acids in the α and β-subunits are located in (β/α)8-barrel of domain II. The β-subunit is colored gray, with residues of the active site distinguished in orange. The GM2-activator protein complex (GM2-AP) docks into a large groove between the two subunits so that the terminal non-reducing GalNAc sugar on GM2 can be presented to the α-subunit active site and removed. Two surface loops (magenta and green), present only on the α-subunit, interact with the docked activator protein and appear to be involved in creating a docking site unique to the α-subunit. The magenta colored loop is proteolytically removed from the b-subunit during post-translational processing and may represent a modification that regulates the metabolic function of this subunit. (c) Model of the GM2 oligosaccharide (yellow) bound to the α-subunit active site (gray). The distorted boat conformation of the terminal GalNAc to be removed (Gal, labeled in blue) and the pseudoaxial orientation of the scissile bond and leaving group are based on crystallographic observations of the Michaelis complex of chitobiose bound to SmCHB.20 By incorporating these conformational restraints into the model, only one reasonable position could be found for the sialic acid residue (labeled SIA) within the active site pocket. Once positioned, the negatively charged carboxylate of the sialic acid, which can only be accommodated by the α-subunit, was found to come within hydrogen bonding distance of Arg424, a positively charged residue that is unique to the α-subunit (the b-subunit contains a Leu at this position). αGlu394 and αAsn423 (which are both Asp residues in the b-subunit) are believed to help hold Arg424 into position. Arg424, in turn, stabilizes the negatively charged carboxylate of the sialic acid of the substrate via electrostatic and hydrogen-bonding interactions. The general acid-base residue, Glu323 (Glu355 in the β-subunit), can be seen interacting with the glycosidic oxygen atom of the scissile bond. Hexosaminidase α-subunits are known in many species. The native human sequence (P06865) was compared with native sequences and the percent sequence identity (using BLAST on UniProt with default options including E-Threshold of 10, auto matrix, allowing gaps) is shown in Table 2 below:

TABLE 2

| SPECIES | Uniprot ID | % Sequence Identity |
|---|---|---|
| Mus musculus | P29416 | 84 |
| Rattus norvegicus | Q641X3 | 83 |
| Bos taurus | Q0V8R6 | 84 |
| Felis catus | G4XSV9 | 84 |
| Heterocephalus glaber | G5BHB4 | 81 |
| Struthio camelus australis | A0A093HGG6 | 74 |
| Cuculus canorus | A0A091H728 | 73 |

A pair-wise sequence alignment and secondary structure of the native human hexosaminidase α-subunit versus the native human hexosaminidase β-subunit is shown in FIG. 8. Residues colored in light blue are removed during post-translational processing, and residues in italics compose the ER signal peptides of each subunit (Table 4). Sites (N-X-S/T) known to contain N-linked oligosaccharides are underlined, and glycan sites that receive the mannose-6-phosphate lysosomal targeting moiety are doubly underlined (Table 4). Primary sequence corresponding to the mature, lysosomal ap and by chains are surrounded by square brackets, sequence comprising chains am and bb are in curly brackets, and the sequence for chain ba is surrounded by normal brackets. Secondary structural elements are as follows: α-helices are drawn as green boxes, β-strands are drawn as blue arrows and disulfide bridges are shown by blue-gray lines connecting Cys residues. Residues boxed in yellow are involved in subunit dimerization as determined from the Hex B crystal structure and also predicted for the Hex A isozyme. The unique mature α-subunit loops 280-283 (GSEP) and 396-398 (IPV) are colored magenta and are predicted to interact directly with the bound activator protein. β-subunit point mutations known to cause GM2-gangliosidosis are indicated directly above the β-subunit sequence in purple.

Sequence identity is typically assessed by the BLAST version 2.1 program advanced search (parameters as above; Altschul, S. F., Gish, W., Miller, W., Myers, E. W. & Lipman, D. J. (1990) "Basic local alignment search tool." J. Mol. Biol. 215:403_410). BLAST is a series of programs that are available online through the U.S. National Center for Biotechnology Information (National Library of Medicine Building 38A Bethesda, Md. 20894) The advanced Blast search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656).

In one embodiment, the variant hexosaminidase α-subunit described herein includes mature forms of the polypeptide. For example, cellular processing and mature forms of the α-subunit of human β-hexosaminidase B are described in Mark et al. "Crystal Structure of Human β-Hexosaminidase B: Understanding the Molecular Basis of Sandhoff and Tay-Sachs Disease", Journal of Molecular Biology Volume 327, Issue 5, 11 Apr. 2003, Pages 1093-1109. Processing and post-translational modifications of the variant α-subunit described herein is expected to be similar to that of the naturally occurring α-subunit. In one embodiment, the variant α-subunit described herein does not contain an N-terminal signal sequence or is cleaved to remove an N-terminal signal sequence. In one embodiment, the variant α-subunit does not contain the signal peptide set forth in amino acids 1 to 22 and/or the peptide region set forth in amino acids S75 to H88 of SEQ ID NO: 1 or SEQ ID NO: 2. In one embodiment, the variant α-subunit has sequence identity to, comprises, consists essentially of or consists of the mature form of the amino acid sequence set forth in SEQ ID NO: 2. In one embodiment, the variant α-subunit includes one or more one or more post-translational modifications, including proteolytic and/or glycolytic processing. For example, in one embodiment the variant α-subunit is glycosylated at selected Asn-X-Ser/Thr, optionally followed by the addition of one or two phosphate markers to one or more high mannose-type oligosaccharide. In one embodiment, the variant α-subunit described herein is produced recombinantly or synthetically in order to include one or more features of the mature form of the protein.

The variant hexosaminidase α-subunit described herein can be prepared using different methods known in the art for producing polypeptides. For example, in one embodiment the variants are prepared using recombinant techniques such as by modifying and/or expressing a nucleic acid molecule that encodes for the variant polypeptide. Various recombinant technologies including but not limited to those disclosed by Sambrook et al (Sambrook J et al. 2000. Molecular Cloning: A Laboratory Manual (Third Edition), Cold Spring Harbor Laboratory Press) are also suitable for preparing the peptides described herein. In one embodiment, the variant hexosaminidase α-subunit described herein is produced in a mammalian cell expression system. In one embodiment, the mammalian cell expression system results in the post-translation processing of the variant hexosaminidase α-subunit expressed therein. Optionally, the variant hexosaminidase α-subunit as described herein is produced in a mammalian cell expression system that results in the glycosylation of the polypeptide. The variant polypeptides of the invention are also readily prepared by chemical synthesis using techniques well known in the art related to the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). Accordingly, in one embodiment, the variant hexosaminidase α-subunit described herein is a recombinant protein. In one embodiment, the variant hexosaminidase α-subunit described herein is a synthetic protein.

In one embodiment, there is also provided a method for producing a variant hexosaminidase α-subunit as described herein. In one embodiment, the method comprises the recombinant expression of a nucleic acid molecule encoding the variant hexosaminidase α-subunit. For example, in one embodiment the method comprises culturing a host cell transfected with a vector encoding a variant hexosaminidase α-subunit under conditions suitable for the expression of the variant hexosaminidase α-subunit. Optionally, the host cell is a mammalian host cell or a host cell selected to ensure the post-translational modification of the variant hexosaminidase α-subunit. In one embodiment, the variant hexosaminidase α-subunit is glycosylated by the host cell. In one embodiment, the host cell produces mature forms of the variant hexosaminidase α-subunit. In some embodiments, the method further comprises isolating the variant hexosaminidase α-subunit or a protein complex comprising the variant hexosaminidase α-subunit from the host cell or culture medium.

In one embodiment, the variant hexosaminidase α-subunit described herein comprises an amino acid sequence that has been modified to reduce immunogenicity of the protein. For example, in one embodiment, computer modeling of the amino acid sequence of the variant α-subunit is used to identify and change one or more of the amino acid residues to minimize epitope recognition by the immune system. In one embodiment, the amino acid sequence of the variant hexosaminidase α-subunit described herein is modified to reduce the probability of an undesirable immune response when administered to a subject or used for the treatment of GM2 gangliosidosis. Examples of methods useful for reducing the immunogenicity of a protein include those described in Bryson et al. "Prediction of immunogenicity of therapeutic proteins: validity of computational tools." BioDrugs. 2010 Feb. 1; 24(1):1-8; and Perry et al. "New approaches to prediction of immune responses to therapeutic proteins during preclinical development Drugs R D. 2008; 9(6):385-96.

In another aspect, the present disclosure provides nucleic acid molecules that encode for a variant hexosaminidase α-subunit as described herein. For example, in one embodiment the nucleic acid molecule encodes for a polypeptide that has sequence identity to the exemplary variant hexosaminidase α-subunit set forth in SEQ ID NO: 2, or to mature forms of said protein. For example, in one embodiment, the nucleic acid molecule comprises, consists essentially or, or consists of a sequence that encodes for a polypeptide that has at least 30%, 40%, 50%, 60%, 70%, 80%, 85%, 90%, 95% or 97% sequence identity to SEQ ID NO: 2, or to mature forms of said protein. In one embodiment, the nucleic acid molecule encodes for a variant hexosaminidase α-subunit with one or more substitutions or deletions listed in Table 4. A codon optimized nucleic acid sequence for the exemplary variant hexosaminidase α-subunit is shown in FIG. 3 and identified as SEQ ID NO: 3. Accordingly, in one embodiment, the nucleic acid molecule comprises, consists essentially or, or consists of a sequence that has at least 30%, 40%, 50%, 60%, 70%, 80%, 85%, 90%, 95 or 97% sequence identity to SEQ ID NO: 3. In one embodiment, the sequence of the nucleic acid molecule is codon-optimized for expression in a particular host cell, such as a mammalian host cell.

A nucleic acid molecule as described herein can be generated using recombinant techniques, such as by selectively amplifying a nucleic acid using the polymerase chain reaction (PCR) methods and cDNA or genomic DNA and then introducing modifications to said nucleic acid molecule. A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

In one embodiment, there is also provided a vector comprising one or more nucleic acids encoding a variant hexosaminidase α-subunit as described herein. Optionally, the nucleic acid is a DNA molecule or an RNA molecule. These nucleic acid molecules are readily incorporated according to procedures known in the art into an appropriate expression vector that ensures suitable expression of the polypeptide in a cultured cell system, such as for producing and then isolating the variant polypeptide in vitro for use in enzyme replacement therapy. Alternatively, the sequence could be incorporated into a virus; such as replication defective retrovirus, adenovirus, adeno-associated virus, lentivirus, herpes simplex virus, and pox virus or any other suitable vector for in vivo or ex vivo gene therapy. Expression vectors include, but are not limited to, cosmids, plasmids, or modified viruses (e.g., replication defective retroviruses, adenoviruses and adeno-associated viruses etc.), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" means that the nucleic acid is linked to regulatory sequences in a manner that allows expression of the nucleic acid. In one embodiment, the vector is suitable for use in gene therapy for the treatment of GM2 gangliosides.

Along with enzyme replacement therapy, gene therapy for TSD and SD is another therapeutic approach that is currently being investigated. Proof-of-concept gene transfer experiments have demonstrated the potential for long-term therapeutic rescue of GM2 ganglioside accumulations and improvement of disease symptoms in mouse models for SD or TSD. Adeno-associated virus (AAV) vectors have been utilized in over 75 gene transfer clinical trials because of their excellent safety record, relatively low immunogenicity, and ability to confer long-term expression of the delivered transgene. Recently, widespread central nervous system (CNS) gene transfer has been demonstrated in feline, porcine, and non-human primate animal models, suggesting the possibility for a translatable gene transfer approach for disorders such as Tay-Sachs disease using AAV vectors.

A major limitation for AAV is its packaging capacity, which is approximately 4.5 kb of foreign DNA for traditional single-strand AAV, and approximately 2.1 kb for the more efficient self-complementary AAV. The coding DNA sequence for the α-subunit of Hex A is ~1.6 kb, and ~1.7 kb for the β-subunit, to which other 3' and 5' sequences must be added for efficient expression by infected cells. Packaging the α-subunit is well within the size constraints of the AAV genome. However, overexpression of the α-subunit alone would not lead to an overabundance of the missing heterodimeric Hex A isozyme, since the endogenous β-subunit would become limiting in this scenario. For effective therapy Hex A is preferably overexpressed as this leads to secretion of the excess enzyme, which can then cross-correct other, non-infected cells through recognition and up-take into their lysosomes by their plasma membrane mannose-6-phosphate receptors. Packaging both of these subunits within a single AAV genome, along with the transcriptional regulator elements necessary to drive expression, is impractical due to size constraints.

For example, in one embodiment, the vector is an adeno-associated viral (AAV) vector. In one embodiment, the vector is able to cross the blood brain vector, such as AAV9. In one embodiment, the vector is a lentiviral vector. For example, in one embodiment a lentiviral vector is used to transfer a nucleic acid molecule encoding a variant hexosaminidase α-subunit into hematopoietic stem cells, which then can be administered to a subject as a means of ex vivo gene therapy. The embodiments described herein include other vectors known in the art to be useful for the recombinant expression of proteins and/or gene therapy.

In one embodiment, the nucleic acid molecule encoding a variant hexosaminidase α-subunit as described herein, or a vector comprising said nucleic acid molecule, is conjugated to a molecule that facilitates entry of the nucleic acid molecule or vector into the cell. In one embodiment, the nucleic acid molecule or vector is conjugated to a cell penetrating peptide. For example, in one embodiment, nucleic acid molecule or vector is conjugated to a cell penetrating peptide selected from TAT, Angiopep, penetratin, TP, rabies virus glycoprotein (RVG), prion peptide, and SynB. In one embodiment, the nucleic acid molecule or vector is conjugated to the atoxic fragment C of tetanus toxin (TTC). Alternatively or in addition, the nucleic acid molecule or vector may be conjugated to a peptide or other molecule that facilitates crossing the blood brain barrier. Various conjugates useful for facilitating crossing the blood brain barrier are known in the art including but not limited to those described in Reinhard Gabathuler, Neurobiology of Disease 37 (2010) 48-57; Spencer B J, and Verma I M, Proc Natl Acad Sci USA. 2007 May 1; 104(18):7594-930; Coloma et al., Pharm Res. 2000 March; 17(3):266-74; and Dobrenis et al, Proc. Natl. Acad. Sci. USA Vol. 89, pp. 2297-2301, March 1992. In one embodiment, the nucleic acid molecule or vector is conjugated to the lipoprotein receptor-binding domain of apolipoprotein-B (ApoB-BD). In one embodiment, the nucleic acid molecule or vector is conjugated to a peptide binding domain associated with the transferrin receptor or insulin-like growth factor receptor.

In one embodiment, there is provided a pharmaceutical composition comprising a variant or protein complex as described herein and a pharmaceutically acceptable carrier. In an embodiment, there is also provided a pharmaceutical composition comprising a nucleic acid molecule encoding a variant or protein complex as described herein and a pharmaceutically acceptable carrier. In one embodiment, the pharmaceutical composition comprises a vector, such as a vector suitable for gene therapy. In one embodiment, there is provided a host cell transfected with a nucleic acid molecule or vector encoding a variant polypeptide as described herein.

The isolated proteins, nucleic acid molecules or host cells of the invention are optionally formulated into a pharmaceutical composition for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. One aspect of the disclosure also includes the use of the variants, protein complexes, nucleic acid molecules or host cells of the invention for the treatment of GM2 gangliosidosis or for the preparation of a medicament for the treatment of GM2 gangliosidosis.

The isolated proteins, nucleic acid molecules, vectors, host cells or pharmaceutical compositions of the invention can be administered to a subject by a variety of methods including, but not restricted to topical administration, oral administration, aerosol administration, intratracheal instillation, intraperitoneal injection, injection into the cerebrospinal fluid including intracerebroventricular, intrathecal, and intracisternal injections, intravenous injection, intramuscular injection, brain or spinal cord intraparenchymal injections, and subcutaneous injection. Dosages to be administered depend on patient needs, on the desired effect and on the chosen route of administration. Nucleic acid molecules and polypeptides may be introduced into cells using in vivo delivery vehicles such as liposomes. They may also be introduced into these cells using physical techniques such as microinjection and electroporation or chemical methods such as co-precipitation, pegylation or using liposomes. Nucleic acid molecules may also be delivered directly to a subject such as by using "naked DNA" delivery techniques. Optionally, the nucleic acid molecules or peptides are introduced into host cells ex vivo and then administered to a subject.

The pharmaceutical compositions can be prepared by known methods for the preparation of pharmaceutically acceptable compositions which can be administered to subjects. In an embodiment, an effective quantity of the nucleic acid molecule or peptide is combined in a mixture with a pharmaceutically acceptable carrier. Suitable carriers are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the substances in association with one or more pharmaceutically acceptable carriers or diluents, and may be contained in buffered solutions with a suitable pH and/or be iso-osmotic with physiological fluids.

On this basis, the pharmaceutical compositions provided herein optionally include an active compound or substance, such as a protein complex as described herein that hydrolyzes GM2 ganglioside, in association with one or more pharmaceutically acceptable carriers, such as a vehicle or diluent, and contained in buffered solutions with a suitable pH and iso-osmotic with the physiological fluids. The methods of combining the active molecules with the vehicles or combining them with diluents are well known to those skilled in the art. The composition optionally includes a targeting agent for the transport of the active compound to specified sites within tissue.

Optionally, the pharmaceutical composition comprises a variant hexosaminidase α-subunit, nucleic acid or vector encoding the same, or a variant protein complex that hydrolyzes GM2 ganglioside as described herein in a formulation with one or more molecules that facilitate transport of the composition across the cell membrane or across the blood brain barrier.

Methods for Hydrolyzing GM2 Ganglioside

Figure 7:
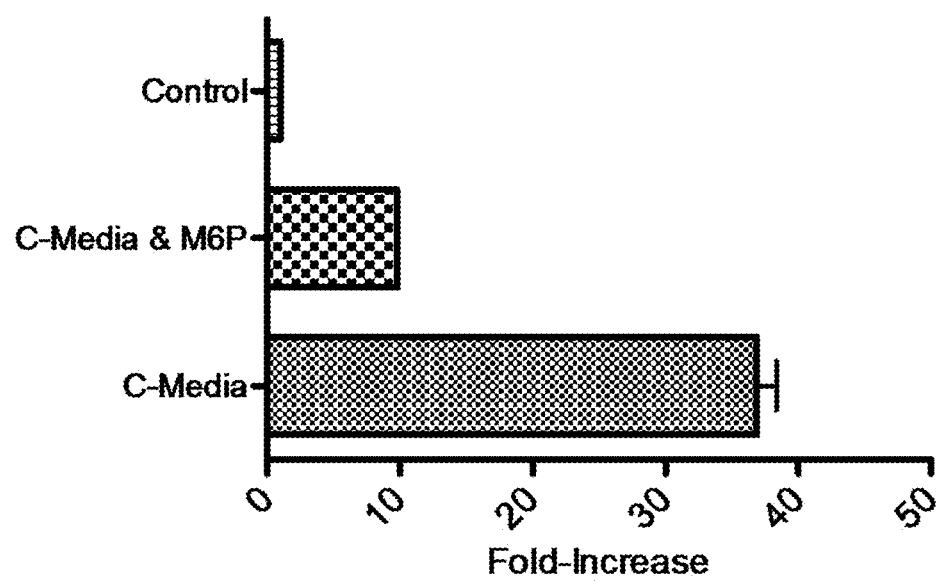

In one aspect of the disclosure there is provided a method for hydrolyzing GM2 ganglioside. As set out in Example 1, protein complexes comprising the variant hexosaminidase α-subunit described herein are able to hydrolyze GM2 ganglioside to produce GM3 ganglioside in the presence of GM2AP. Accordingly, in one embodiment the method comprises contacting a cell with a variant hexosaminidase α-subunit or protein complex comprising a variant hexosaminidase α-subunit as described herein. Optionally, the method comprises transfecting or transducing a cell with a nucleic acid molecule encoding a variant hexosaminidase α-subunit as described herein. The cell may be in vitro, in vivo or ex vivo. In one embodiment, the cell is a brain cell such as a glial cell or neuronal cell or a peripheral neuronal cell such as a cell forming part of the autonomic nervous system. In one embodiment, the cell has a lysosomal accumulation of GM2. In one embodiment, the cell has a mutation associated with GM2 gangliosidosis, optionally Tay-Sachs disease or Sandhoff disease. In one embodiment, the cell has a Hex A deficiency. In one embodiment the Hex A deficient cell can be a liver or bone marrow cell. In one embodiment, cells transfected or transduced with a nucleic acid molecule encoding a variant hexosaminidase α-subunit may overexpress the variant causing much of it to be secreted. As shown in FIG. 7, the secreted variant can then be re-captured by non-infected, deficient cells facilitating their hydrolysis of GM2 ganglioside.

Treatment of GM2 Gangliosidosis and/or β-Hexosaminidase A Deficiencies

In one aspect of the disclosure, there are provided methods for the treatment of GM2 gangliosidosis and associated uses of the products and compositions described herein for the treatment of GM2 gangliosidosis in a subject in need thereof.

As used herein, and as well understood in the art, "to treat" or "treatment" is an approach for obtaining beneficial or desired results, including clinical results. Beneficial or desired clinical results can include, but are not limited to, alleviation or amelioration of one or more symptoms or conditions, such as increasing the level of GM2 ganglioside hydrolysis in the lysozymes of a subject with GM2 gangliosidosis or a reduction in the level or number of symptoms experienced by a subject with GM2 gangliosidosis.

In one embodiment, the method comprises administering to the subject a variant hexosaminidase α-subunit, or a protein complex comprising a variant hexosaminidase α-subunit as described herein. Also provided is the use of a variant hexosaminidase α-subunit or a protein complex comprising a variant hexosaminidase α-subunit as described herein for the treatment of GM2 gangliosidosis in a subject in need thereof. For example, in one embodiment, the products, compositions and methods described herein are useful for enzyme replacement therapy in a subject with a β-hexosaminidase A deficiency.

In one embodiment, the method comprises administering to the subject a nucleic acid molecule encoding a variant hexosaminidase α-subunit as described herein for the treatment of a subject with GM2 gangliosidosis. Also provided is the use of a nucleic acid molecule or vector encoding a variant hexosaminidase α-subunit as described herein for the treatment of GM2 gangliosidosis. For example, in one embodiment, the cells of a subject are transfected with a nucleic acid molecule or transduced with a vector as described herein in order to express the variant hexosaminidase α-subunit in the cells of the subject, commonly known as "gene therapy". In one embodiment, the variant hexosaminidase α-subunit forms a protein complex within the infected cells and is transported to the lysozyme and hydrolyzes GM2 ganglioside. In one embodiment the infected cell expresses high levels of the variant the results in it secretion in a form that can be re-captured by other, non-infected, deficient cells, incorporated into their lysosomes and hydrolyze stored GM2 ganglioside.

The administration or uses of a product or composition as described herein for the treatment of GM2 gangliosidosis can be in vivo and/or ex vivo. In one embodiment, the amount of product or composition that is used, formulated for use or administered to a subject is a therapeutically active amount at dosages and for periods of time necessary to achieve the desired result, namely the treatment of GM2 gangliosidosis. For example, a therapeutically active amount of a product of composition may vary according to factors such as the disease state, age, sex, and weight of the individual, and the ability of the substance to elicit a desired response in the individual. Formulations and/or dosage regimes may be adjusted to provide the optimum therapeutic response. For example, several divided doses may be administered daily or the dose may be proportionally reduced as indicated by the exigencies of the therapeutic situation. In one embodiment, dosages may be administered using intravenous infusions on a weekly or biweekly basis. Optionally, the variant protein or pharmaceutical composition described herein may be formulated for use and/or administered directly to the CNS by continuous or periodic bolus injections from or through an implanted pump, such as those described in U.S. Pat. No. 8,419,710.

Table 3 below shows residues comprising the dimer interfaces in HexA and HexB based on a PISA (Proteins, Interfaces, Structures and Assemblies) interface analysis.

TABLE 3

Residues of Dimer Interfaces

| Alpha subunit | Beta subunit |
|---|---|
| R178 | R211 |
| H179 | H212 |
| Y180 | Y213 |
|  | P215 |
|  | K217 |
| P209 | Q242 |
| Y227 | Y260 |
| N228 | S261 |
| T231 | S263 |
| H232 | H264 |
| N423 | D452 |
| R424 | L453 |
| I425 | I454 |
| S426 | S455 |
| Y427 | Y456 |
| G428 | G457 |
| P429 | Q458 |
|  | G490 |
| E462 | E491 |
| Y463 | Y492 |
| V464 | V493 |
| D465 | D494 |
|  | A495 |
| T467 | T496 |
| N468 | N497 |
| P471 | P500 |
| R472 | R501 |
| R504 | R533 |
| L508 | V537 |
| Q513 | A542 |
| A514 | A543 |
| Q515 | Q544 |
| P516 | P545 |
| L517 | L546 |
| N518 | Y547 |
| V519 | A548 |
| G520 | G549 |
| F521 | Y550 |
| C522 | C551 |
| E523 | N552 |
| E525 |  |
| F526 |  |
| E527 |  |
| Q528 |  |

EXAMPLES

The following examples illustrate embodiments of the invention and do not limit the scope of the invention.

Example 1: Construction and Testing of a Variant β-Hexosaminidase

A series of 21 substitutions and a deletion were made in the cDNA encoding the α-subunit of β-Hexosaminidase. The substitutions represented nucleotides that encode residues uniquely found in the β-subunit, while the deletion targeted one codon for an α-residue not encoded in the β-subunit (Table 4, FIG. 1). Based on an analysis of the HexA and HexB crystal structures and molecular modeling, these amino acids were predicted to be involved in either the formation of the stable Hex B (β-homodimer) subunit-subunit interface or that area of the β-subunit that along with other areas in the α-subunit, allows heterodimeric Hex A to form the active quaternary complex with the GM2-GM2AP complex (FIG. 2). Thus, the resulting variant α-subunit was predicted to form a very stable homodimer, like Hex B, which, like heterodimeric Hex A, can hydrolyze GM2 using GM2AP as a substrate-specific co-factor.

As set out below, the variant protein with the modifications listed in Table 4 was demonstrated to form a homodimer and hydrolyze GM2 ganglioside in the presence of the human GM2 activator protein GM2AP.

Materials and Methods

Plasmid Construct:

The β-Hexosaminidase variant α-subunit) were codon-optimized for mouse and human expression by DNA2.0 (Menlo Park, Calif.). The coding DNA sequences were cloned into the pJ603 mammalian expression vector (DNA2.0), which drives the Hex subunit expression via the CMV promoter and also co-expresses the neomycin resistance gene (FIG. 3).

Cell Lines and Tissue Culture:

An immortalized human Tay-Sachs Glial cell line was obtained from R. A. Gravel. Human Tay-Sachs skin fibroblasts were obtained from the Hospital For Sick Children tissue culture facility. All cells were grown in alpha-minimal essential medium from Wisent Inc. (Canada) in the presence of 1% antibiotics (penicillin and streptomycin, Gibco BRL, Canada) and supplemented with Fetal Bovine Serum (FBS) (Wisent Inc., Canada) at 10% and incubated at 37° C. in a humidified atmosphere with 5% $CO_2$.

Chemicals and Hex Assay:

Because of the complexity of assaying Hex activity with its natural substrate (the GM2-GM2AP complex), simple fluorescent artificial substrates were introduced that are hydrolyzed by Hex in a GM2AP-independent manner. The oldest is neutral 4-methylumbelliferyl-2-acetamido-2-β-D-glucopyranoside (MUG). However, when MUG is used to assay total Hex activity in TSD cells, nearly normal enzyme levels are obtained, because of increased levels of Hex B. A newer, more specific, negatively charged version of MUG, 4-methylumbelliferyl-2-acetamido-2-deoxy-β-D-glucopyranoside-6-sulfate (MUGS), was developed that is only poorly bound and hydrolyzed by Hex B and can thus be used directly to diagnose TSD. In SD both Hex A and B are deficient, but a small amount of Hex activity (~2% of normal, as measured by MUG) persists due to the inefficient dimerization of α-subunits to produce an unstable acidic isozyme, Hex S (α monomers that fail to dimerize are cleared by the endoplasmic reticulum associated degradation system). While human Hex S, like Hex B, is unable to interact with the GM2-GM2AP complex, it can hydrolyze MUGS more efficiently than Hex A because it possesses two α-active sites. The ~MUG/MUGS ratios of the Hex isozymes are: Hex B, ~300/1; Hex A, 3-4/1; and Hex S, 1-1.5/1.

The synthetic fluorogenic substrates, MUGS, used to assay Hex A-like activity (e.g. Hex S and the variants) and MUG, used to assay total Hex activity, obtained from Toronto Research Chemicals (Canada), were used as previously reported in Tropak et al., (2004) Pharmacological enhancement of β-hexosaminidase activity in fibroblasts from adult Tay-Sachs and Sandhoff patients. J Biol Chem 279: 13478-13487. CBE, a covalent inhibitor of glucocerebrosidase, was from Toronto Research Chemicals (Canada). Cholesterol, purchased from Sigma-Aldrich (Canada), phosphatidyl choline (egg) and phosphatidyl inositol (bovine liver) from Avanti Polar Lipids (USA), and polycarbonate 100 nm filters from Avestin, Inc. (Canada), were used to produce the previously described (Tropak et al., (2010) A sensitive fluorescence-based assay for monitoring GM2 ganglioside hydrolysis in live patient cells and their lysates. Glycobiology 20: 356-365) negatively-charged liposomes that the NBD-GM2 substrate was incorporated into for the in vitro Hex assays (see below). Recombinant GM2AP was expressed in *Escherichia coli* then purified (His6-tagged) and re-folded.

In cellulo NBD-GM2 assays were performed using the fluorescent GM2 derivative, NBD-GM2, as previously reported (Tropak et al., (2010) A sensitive fluorescence-based assay for monitoring GM2 ganglioside hydrolysis in live patient cells and their lysates. Glycobiology 20: 356-365). Briefly, confluent transfected or non-transfected cells in 10 cm plates were grown for 18 h in FBS-free media containing NBD-GM2 (4.7 μg mL$^{-1}$) and CBE (50 μM). After media removal, the cells were rinsed with PBS and incubated with media containing 5% FBS for an additional 2 hr before harvesting. The differential extraction of the acidic gangliosides and neutral glycolipids from each cell suspension was done according to the procedure described by Folch (Folch J, Lees M, Sloane Stanley G H (1957) A simple method for the isolation and purification of total lipids from animal tissues. J Biol Chem 226: 497-509). The extracts were then cleaned using C-18 Zip Tips and prepared for glycolipid separation by high performance thin layer chromatography (HPTLC) as previously reported. Bands corresponding to NBD-glycolipid derivatives were visualized and quantified using the Storm Imager.

In vitro NBD-GM2 assay were carried out with aliquots containing 150 nmoles (MUG)/hr of total Hex activity from the DEAE ion-exchange separated variant α-subunit homodimer (see below) or purified Hex A and Hex B from human placenta. Each isozyme was incubated overnight in McIlvaine's citrate phosphate buffer (pH 4.1) containing NBD-GM2 incorporated into negatively-charged liposomes plus rGM2AP, in a total reaction volume of 50 μL. The glycolipids (both acidic and neutral) were bound in a C-18 Zip tip, washed with water, eluted with 100% methanol and concentrated by drying before their separation by HPTLC.

Western Blotting:

Lysates from human WT fibroblasts and human TSD Glial cells were subjected to SDS-PAGE on a 10% bis-acrylamide gel, transferred to nitrocellulose, and processed as described in Hou et al. (1998) A Pro$^{504}$Ser substitution in the β-subunit of β-hexosaminidase A inhibits α-subunit hydrolysis of G$_{M2}$ ganglioside, resulting in chronic Sandhoff disease. J Biol Chem 273: 21386-21392. Blots were incubated with a rabbit polyclonal IgG against purified human Hex A, followed by a horseradish peroxidase-conjugated, goat, anti-rabbit IgG secondary antibody, developed using chemiluminescent substrate according to the manufacturer's protocol (Amersham Biosciences, UK) and recorded on BIOMAX x-ray film (Kodak).

Ion-Exchange Chromatography:

DEAE Sepharose CL-6B (Pharmacia), 250 μL, was pre-equilibrated in a small column with 10 mM phosphate buffer pH 6.0 containing 25 mM NaCl and 5% glycerol. Cells from two 15 cm plates were harvested and lysed by repeated freeze-thawing in the above 10 mM phosphate buffer. The lysates, 500 μL, were clarified by centrifugation, passed through individual DEAE columns and collected as the flow through fraction. The column was washed with a further 1.5 mL. The column was then eluted with 1.5 mL of the phosphate buffer containing 150 mM NaCl, followed by another 1 mL wash with the same buffer. Finally the columns were eluted with 1.25 mL of buffer containing 500 mM NaCl to collect the α-derived hybrid homodimers, followed by a final 1 mL wash. All the fractions were assayed with MUGS.

Results

The construct encoding the variant α-subunit was transiently expressed in a human infantile TSD Glial cell line, and confirmed to express the variant polypeptide and exhibit increased levels of MUGS hydrolysis. These cells were then placed in medium containing neomycin for selection. Neomycin-resistant mix colonies were produced and individual clonal colonies isolated and expanded in order to select for colonies that stably express the construct. The specific activity (nmoles (MUG)/mg protein) of the mixed colonies was 8,000 fold higher than untransfected TSD Glial cells and 100 times higher than normal human fibroblasts. As shown in Table 5, the individual clonal colonies produced specific activities up to twice as high as the mixed colonies. Previously, specific activity data was obtained from screening over 200 clonal cell populations stably expressing either of two β-derived hybrids and only one clone was identified that expressed specific activity levels ~7-fold higher than wild-type fibroblasts. The initial mix colonies expressed specific activity levels ~10-fold lower than wild-type fibroblasts. Since all of these constructs were codon optimized and expressed in the same vector, it can be concluded that the present variant hexosaminidase α-subunit is better able to fold and dimerize into a functional Hex isozyme than either of the previous two β-derived hybrids described in Sinici et al., (2013) In cellulo examination of a β-α hybrid construct of β-hexosaminidase A subunits, reported to interact with the GM2 activator protein and hydrolyze GM2 ganglioside. PLoS One 8: e57908

Three clonal colonies that were found to highly express the variant protein were incubated in media containing NBD-GM2, (which is concentrated in lysosomes through endocytosis) for 18 hr, washed, lysed and Folch-extracted to produce an upper aqueous phase and a lower organic (chloroform) phase. The upper phase, enriched in acidic glycolipids, and the lower phase, enriched in neutral glycolipids, were analyzed by HPTLC (FIG. 4). Because this is a live cell-based assay NBD-GM2 hydrolysis into NBD-GM3 is rapidly followed by the hydrolysis of NBD-GM3 into lactosylceramide (NBD-LacCer) and then glucosylceramide (NBD-GlcCer). Hydrolysis of NBD-GlcCer to NBD-ceramide (NBD-Cer) is strongly inhibited by the addition of a covalent inhibitor of glucocerebrosidase, conduritol-B-epoxide, CBE. All three colonies of cells stably expressing the construct produced much higher levels of NBD-GM3, NDB-LacCer and particularly NBD-GlcCer than did untransfected cells (FIG. 4). These data indicate that the variant protein can correct TSD cells either acting as a homodimer or possibly as a β-variant α-subunit heterodimer. Importantly, the data also demonstrate that the variant protein is transported to the lysosomes of the TSD glial cells where the NBD-GM2 is localized.

Figure 5:
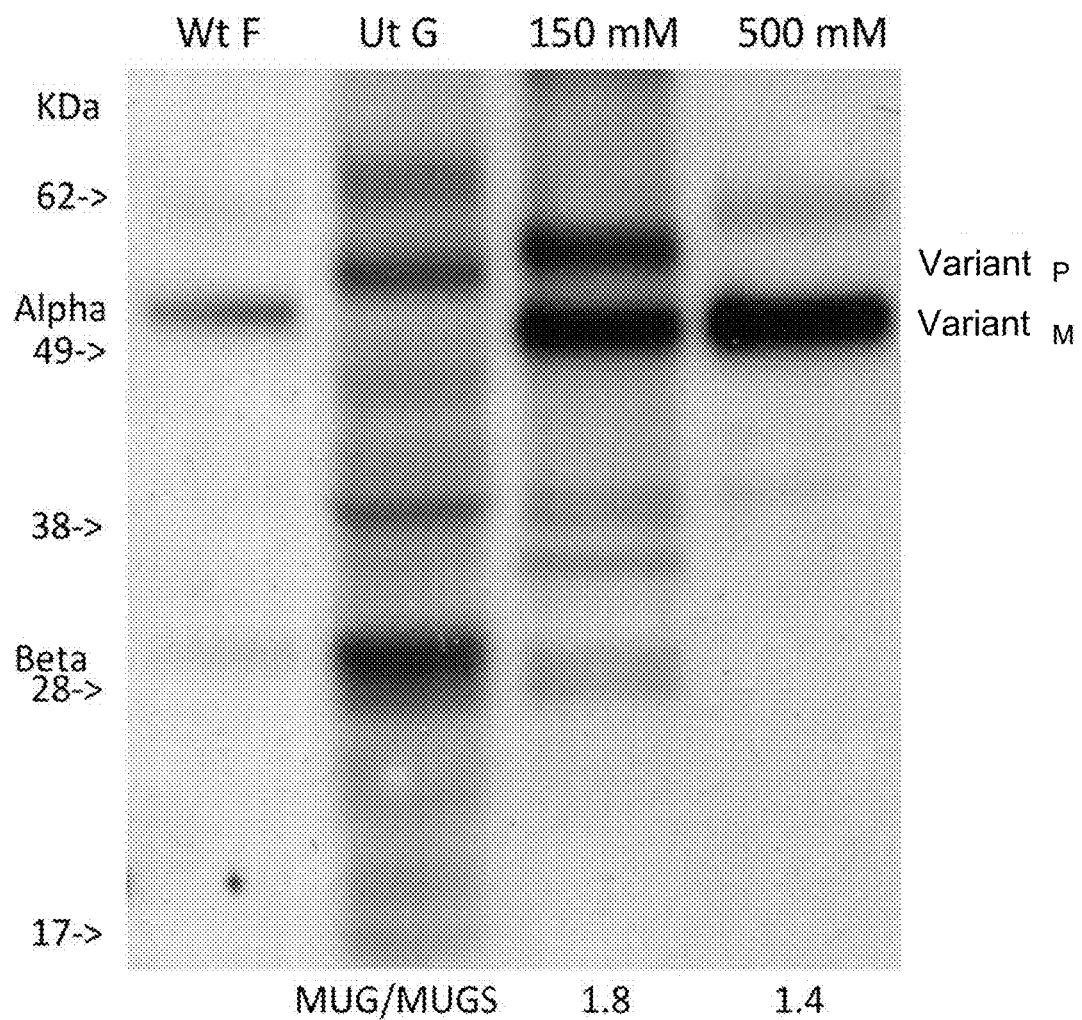
Figure 6:
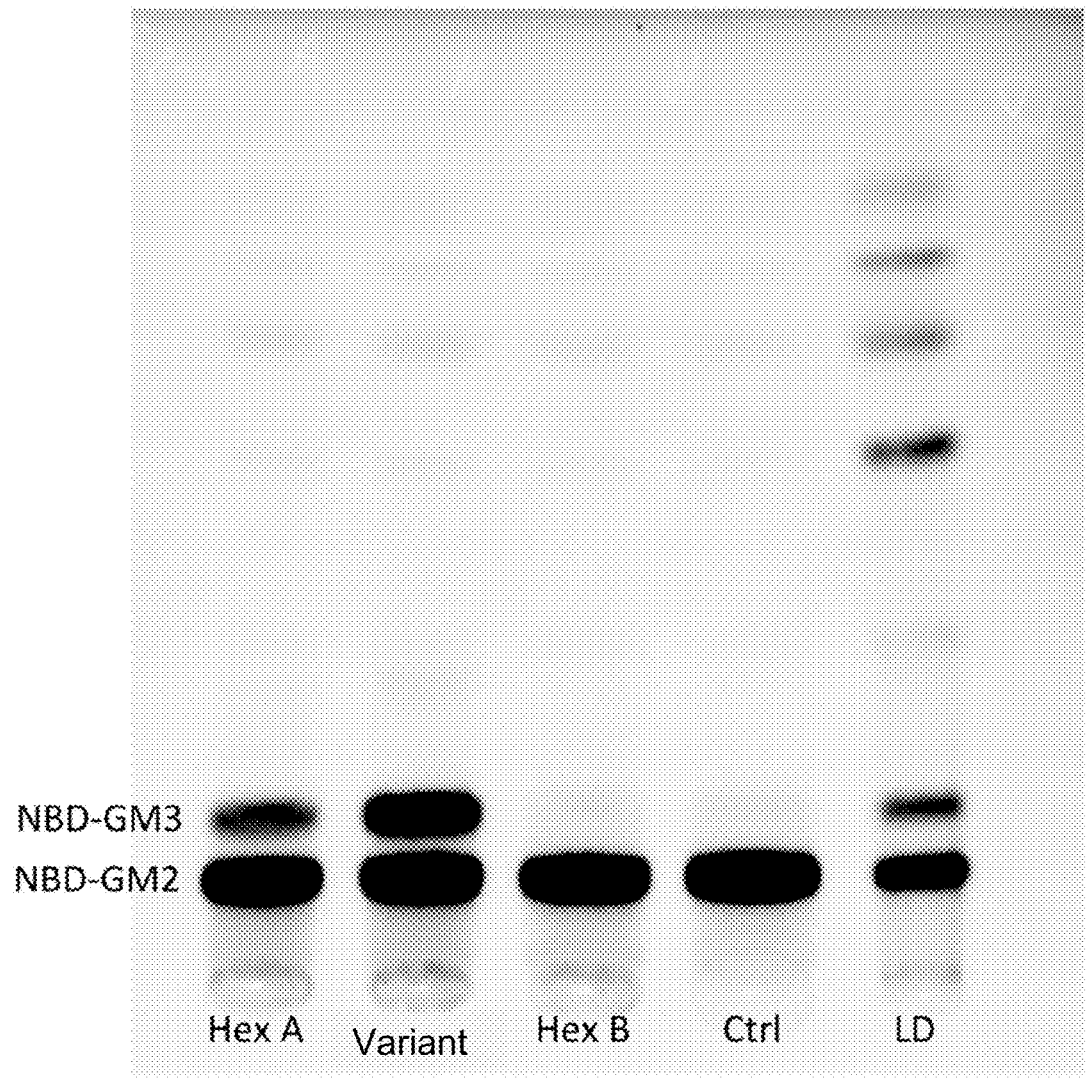

In order to determine the subunit composition of the Hex isozymes responsible for the in cellulo hydrolysis of NBD-GM2, the lysate from permanently expressing TSD Glial cells was separated by DEAE ion-exchange chromatography. Based on the isozymes know or predicted pls, at pH 6 and the 25 mM NaCl initially used in the separation, Hex B will not bind. At pH 6 and 150 mM NaCl any heterodimeric Hex (β-variant α-subunit), as well as the variant α-subunit in its precursor form (during maturation in the lysosome the α-subunit losses several basic residues shifting its pI) should be eluted from the column. At pH 6 and 500 mM NaCl the remaining mature form of the variant α-subunit homodimer should elute. This assessment was confirmed by Western blot analysis of the fractions that contained the peak of Hex activity from the 150 mM and 500 mM stepwise elution of the DEAE column, compared with the banding patterns produced by wild-type human fibroblasts and untransfected TSD Glial cell lysates (FIG. 5). The variant α-subunit homodimer from the 500 mM NaCl elution step was next used in an in vitro assay with the NDB-GM2 contained in negatively charged liposomes in the presence of human GM2AP produced in bacteria. The 150 nmoles (MUG)/hr of total Hex activity from the variant protein fraction was compared to the same number of MUG units of purified Hex A and Hex B (FIG. 6). Only the assay containing Hex A or the variant protein produced detectable levels of NBD-GM3 (further break-down of GM3 is not significantly seen in the in vitro assay). Interestingly, since MUG is hydrolyzed by both the α- and β-active sites and GM2 by only the α-active site, it would be predicted that if the homodimeric variant α-subunits were able to bind and hydrolyze the GM2-GM2AP complex at both its active sites, the same number of MUG units of the variant protein should produce twice as much NBD-GM3 as Hex A. As shown in FIG. 6, it appears that when the same number of MUG units of either the variant protein or Hex A are used in an in vitro assay with NBD-GM2 as the substrate and human rGM2AP as the substrate-specific co-factor, the variant protein produces at least twice as much NBD-GM3 as Hex A.

The variant α-subunit described herein was produced by substituting 21 aligned amino acids unique to the β-subunit of Hex (Table 4, FIG. 1) and deleting αP229, which has no corresponding aligned residue in the β-subunit. The α-subunit and β-subunit of Hex have only about 60% sequence identity, and the selection of the specific residues described herein represents a small percentage of the total differences between the two subunits. These residues were predicted to define the more stable β-subunit-subunit interface, and the area of the β-subunit needed by Hex A (along with another area in the α-subunit) to bind the GM2-GM2AP complex (Table 4, FIG. 2), into the primary structure of the α-subunit (FIG. 1). This produced a variant hexosaminidase α-subunit that, in its homodimeric form (FIG. 5), is transported to the lysosome (FIG. 4) where it can hydrolyze GM2 ganglioside in a human-GM2AP-dependent manner (FIGS. 4 & 6). The cDNA encoding this hybrid subunit is 1,584 bases in size (FIG. 1), which will allow it to be incorporated into AAV for potential gene therapy applications for TSD and SD patients. This construct could also be used to produce Hex for enzyme replacement therapy for these same patients.

TABLE 4

Amino acid changes to the Hex A α-subunit to convert the dimer interface from α to β and to introduce the putative GM2AP binding surface from β-onto the α-subunit. Optionally, residue position 436 may be valine as a result of a known neutral polymorphism and the amino acid change is valine to lysine i.e. V436K.

| Residue position (α numbering) | Change (α to β) | Reason |
|---|---|---|
| 184 | Ser (S) to Lys (K) | Generate β dimer Interface |
| 209 | Pro (P) to Gln (Q) | Generate β dimer Interface |
| 228 | Asn (N) to Ser (S) | Generate β dimer Interface |
| 229 | Pro deleted | Generate β dimer Interface |
| 230 | Val (V) to Leu (L) | Generate β dimer Interface |
| 231 | Thr (T) to Ser (S) | Generate β dimer Interface |
| 429 | Pro (P) to Gln (Q) | Generate β dimer Interface and GM2A binding site |
| 432 | Lys (K) to Arg (R) | GM2A binding site |
| 433 | Asp (D) to Lys (K) | GM2A binding site |
| 436 | Ile (I) or Val (V) to Lys (K) | GM2A binding site |
| 466 | Asn (N) to Ala (A) | Generate β dimer Interface |
| 491 | Ser (S) to Arg (R) | GM2A binding site |
| 493 | Leu (L) to Met (M) | GM2A binding site |
| 494 | Thr (T) to Asp (D) | GM2A binding site |
| 495 | Phe (F) to Asp (D) | GM2A binding site |
| 498 | Glu (E) to Asp (D) | GM2A binding site |
| 508 | Leu (L) to Val (V) | Generate β dimer Interface |
| 513 | Gln (Q) to Ala (A) | Generate β dimer Interface |
| 518 | Asn (N) to Tyr (Y) | Generate β dimer Interface |
| 519 | Val (V) to Ala (A) | Generate β dimer Interface |
| 521 | Phe (F) to Tyr (Y) | Generate β dimer Interface |
| 523 | Glu (E) to Asn (N) | Generate β dimer Interface |

TABLE 5

Specific activity of transfected and control cells

| | Colony[1]-1 | Colony-2 | Colony-3 | Mixed Colonies | UT[2] | Wt Fibroblast[3] |
|---|---|---|---|---|---|---|
| Specific Activity[4] | 26,000 | 31,000 | 43,000 | 23,000 | 2.8 | 220 |
| Fold increase UT | 9,000 | 11,000 | 16,000 | 8,000 | 1 | 79 |
| Fold Increase Wt | 120 | 140 | 200 | 100 | 0.01 | 1 |

[1]Individual neomycin resistance, clonal colonies of transfected human Tay-Sachs Glial cells
[2]Untransfected human Tay-Sachs Glial cells (α-subunit deficient)
[3]Normal (wild type) human fibroblast cells
[4](MUGS) nmoles * hr$^{-1}$ * mg$^{-1}$ (total protein)

TABLE 6

Alternative amino acid changes to the Hex A α-subunit to convert the dimer interface from α to β and to introduce the putative GM2AP binding surface from β-onto the α-subunit.

| Residue position (α numbering) | Change (α to β) | Reason |
|---|---|---|
| 209 | Pro (P) to Gln (Q), Thr (T) or Ser (S) | Generate β dimer Interface |
| 228 | Asn (N) to Ser (S) | Generate β dimer Interface |
| 229 | Pro deleted | Generate β dimer Interface |
| 231 | Thr (T) to Ser (S) | Generate β dimer Interface |
| 429 | Pro (P) to Gln (Q) | Generate β dimer Interface and GM2A binding site |
| 432 | Lys (K) to Arg (R) | GM2A binding site |
| 433 | Asp (D) to Lys (K) or Arg (R) | GM2A binding site |
| 436 | Ile (I) or Val (V) to Lys (K) or Arg (R) | GM2A binding site |
| 491 | Ser (S) to Arg (R) or His (H) | GM2A binding site |
| 494 | Thr (T) to Asp (D) or Glu (E) | GM2A binding site |
| 508 | Leu (L) to Val (V) | Generate β dimer Interface |
| 513 | Gln (Q) to Ala (A) | Generate β dimer Interface |
| 518 | Asn (N) to Tyr (Y) | Generate β dimer Interface |
| 519 | Val (V) to Ala (A) | Generate β dimer Interface |

Example 2: Variant β-Hexosaminidase is Internalized Via Plasma Membrane Mannose-6-Phosphate Receptors Secreted forms of the variant protein are recognized by plasma membrane mannose-6-phosphate receptors of deficient cells and internalized. Infantile Tay-Sachs fibroblasts were grown for 48 hours in conditioned media (C-Media); i.e., media in which Tay-Sachs glial cells, transfected with the expression vector encoding the variant β-Hexosaminidase protein, had previously been grown for three days. Another flask of these cells was also grown in conditioned media containing 5 mM mannose-6-phosphate (C-Media & M6P). Cells were then washed, harvested and lysed. The specific MUGS activity levels (nmoles MU/mg protein) were determined. FIG. 7 shows the "fold-increase" in the specific MUGS activities over that of the control cells grown in non-conditioned media, i.e. 1=no change in MUGS specific activity. Note that the small amount of MUGS activity in the control cells likely represents Hex B (MUG/MUGS=300/1). As shown in FIG. 7, the MUGS activity level of cells grown in conditioned media containing secreted variant protein was significantly higher in the absence of mannose-6-phosphate relative to conditioned media containing mannose-6-phosphate suggesting that the variant protein is internalized via plasma membrane mannose-6-phosphate receptors.

Further Embodiments

In various embodiments, a variant β-hexosaminidase subunit is included wherein the variant β-hexosaminidase subunit forms a homodimer and wherein the homodimer associates with GM2 activator protein to hydrolyze GM2 ganglioside. The variant β-hexosaminidase subunit can form a homodimer that is stable under physiologic conditions. The variant β-hexosaminidase can include an amino acid sequence having at least 80% sequence identity to residues 89-529 of SEQ ID NO: 1, conservative variants thereof, or alpha/beta alignment variants thereof. The variant β-hexosaminidase can include an amino acid sequence having one or more substitutions or deletions at positions corresponding to residues N228, P229, T231, P429, L508, Q513, N518, and V519 of the native β-hexosaminidase α subunit sequence (SEQ ID NO: 1). The variant β-hexosaminidase can include an amino acid sequence having one or more substitutions selected from the group consisting of N228S, T231S, P429Q, L508V, Q513A, N518Y, and V519A of the native β-hexosaminidase α subunit sequence (SEQ ID NO: 1). The variant β-hexosaminidase subunit can have a deletion at a position corresponding to residue 229 of the native β-hexosaminidase α subunit sequence (SEQ ID NO: 1). The variant β-hexosaminidase subunit of can have an amino acid sequence including one or more substitutions at positions corresponding to residues P429 and K432 of the native β-hexosaminidase α subunit sequence (SEQ ID NO: 1). The variant β-hexosaminidase subunit can have an amino acid sequence including one or more substitutions selected from the group consisting of P429Q or K432R of the native β-hexosaminidase α subunit sequence (SEQ ID NO: 1). The variant β-hexosaminidase subunit can have an amino acid sequence including at least three substitutions or deletions at positions corresponding to residues N228, P229, T231, P429, K432, L508, Q513, N518, and V519 of the native β-hexosaminidase α subunit sequence (SEQ ID NO: 1). The variant β-hexosaminidase subunit can have an amino acid sequence including at least five substitutions or deletions at positions corresponding to residues N228, P229, T231, P429, K432, L508, Q513, N518, and V519 of the native β-hexosaminidase α subunit sequence (SEQ ID NO: 1). The variant β-hexosaminidase subunit can have an amino acid sequence including one or more of a substitution at a position corresponding to residue 209 of the native β-hexosaminidase α subunit sequence (SEQ ID NO: 1), the substitution selected from the group consisting of P209Q, P209T and P209S; a substitution at a position corresponding to residue 433 of the native β-hexosaminidase α subunit sequence (SEQ ID NO: 1), the substitution selected from the group consisting of D433K and D433R; a substitution at a position corresponding to residue 436 of the native β-hexosaminidase α subunit sequence (SEQ ID NO: 1), the substitution selected from the group consisting of I436K, I436R, V436K and V436R; a substitution at a position corresponding to residue 491 of the native β-hexosaminidase α subunit sequence (SEQ ID NO: 1), the substitution selected from the group consisting of S491R and S491H; and a substitution at a position corresponding to residue 494 of the native β-hexosaminidase α subunit sequence (SEQ ID NO: 1), the substitution selected from the group consisting of T494D and T494E. The variant β-hexosaminidase subunit can have an amino acid sequence that is between 400 and 550 amino acids in length. The variant β-hexosaminidase subunit can have an amino acid sequence having at least 90% sequence identity to residues 89-528 of SEQ ID NO: 2. The variant β-hexosaminidase subunit can have an amino acid sequence having at least 95% sequence identity to residues 89-528 of SEQ ID NO: 2. The variant β-hexosaminidase subunit can be conjugated to a peptide or other molecule that facilitates crossing the blood brain barrier. The variant β-hexosaminidase subunit can be conjugated to an ApoB binding domain peptide.

In various embodiments, an isolated or recombinant polynucleotide encoding a variant β-hexosaminidase subunit including an amino acid sequence having at least 80% sequence identity to residues 89-529 of SEQ ID NO: 1 can be included, wherein the variant β-hexosaminidase subunit forms a homodimer and wherein the said homodimer associates with GM2 activator protein to hydrolyze GM2 ganglioside. The isolated or recombinant polynucleotide can encode a variant β-hexosaminidase subunit comprising an amino acid sequence having at least 90% sequence identity to residues 89-529 of SEQ ID NO: 1.

In various embodiments, a variant β-hexosaminidase subunit is included that has an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to residues 89-528 of SEQ ID NO: 2.

In various embodiments, a vector is included having a recombinant polynucleotide as described herein.

In various embodiments, a method of treating a subject exhibiting an abnormal cellular accumulation of GM2 ganglioside is included, the method comprising administering a composition comprising a variant β-hexosaminidase subunit as described herein. In various embodiments, the method can include administering an effective amount of a composition comprising a variant β-hexosaminidase subunit as described herein. In various embodiments the method can be directed to treating a subject exhibiting $G_{M2}$ gangliosidosis.

In various embodiments, a method of treating a subject exhibiting an abnormal cellular accumulation of GM2 ganglioside is included, the method comprising administering a composition comprising a recombinant polynucleotide as described herein. In various embodiments, the method can include administering an effective amount of a composition comprising a recombinant polynucleotide as described herein. In various embodiments the method can be directed to treating a subject exhibiting $G_{M2}$ gangliosidosis.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications, and sequences associated with accession numbers are herein incorporated by reference in their entirety to the same extent as if each individual publication, patent or patent application was specifically and individually indicated to be incorporated by reference in its entirety.

We claim:

1. A variant β-hexosaminidase α subunit comprising at least 90% sequence identity to residues 89-528 of SEQ ID NO: 2, the variant comprising one or more substitutions at positions selected from 433, 436, 491 and 494 of the native β-hexosaminidase α subunit sequence (SEQ ID NO: 1), wherein the variant β-hexosaminidase α subunit forms a homodimer and exhibits GM2 ganglioside hydrolysis activity in the presence of GM2-activator protein.

2. The variant β-hexosaminidase α subunit of claim 1, comprising at least 95% sequence identity to residues 89-528 of SEQ ID NO: 2.

3. The variant β-hexosaminidase α subunit of claim 1, comprising at least 98% sequence identity to residues 89-528 of SEQ ID NO: 2.

4. The variant β-hexosaminidase α subunit of claim 1, comprising between 10 and 21 substitutions selected from S184K, P209Q, N228S, V230L, T231S, P429Q, K432R, D433K, I436K or V436K, N466A, S491R, L493M, T494D, F495D, E498D, L508V, Q513A, N518Y, V519A, F521Y and E523N with reference to the native β-hexosaminidase α subunit sequence (SEQ ID NO: 1).

5. An isolated or recombinant polynucleotide encoding a variant β-hexosaminidase α subunit comprising at least 90% sequence identity to residues 89-528 of SEQ ID NO: 2, the variant comprising one or more substitutions at positions selected from 433, 436, 491 and 494 of the native β-hexosaminidase α subunit sequence (SEQ ID NO: 1), wherein the variant β-hexosaminidase α subunit forms a homodimer and exhibits GM2 ganglioside hydrolysis activity in the presence of GM2-activator protein.

6. The isolated or recombinant polynucleotide of claim 5, wherein the variant β-hexosaminidase α subunit comprises at least 95% sequence identity to residues 89-528 of SEQ ID NO: 2.

7. The isolated or recombinant polynucleotide of claim 5, wherein the variant β-hexosaminidase α subunit comprises at least 98% sequence identity to residues 89-528 of SEQ ID NO: 2.

8. The isolated or recombinant polynucleotide of claim 5, wherein the variant β-hexosaminidase α subunit comprises between 10 and 21 substitutions selected from S184K, P209Q, N228S, V230L, T231S, P429Q, K432R, D433K, I436K or V436K, N466A, S491R, L493M, T494D, F495D, E498D, L508V, Q513A, N518Y, V519A, F521Y and E523N with reference to the native β-hexosaminidase α subunit sequence (SEQ ID NO: 1).

9. A variant β-hexosaminidase α subunit comprising at least 98% sequence identity to residues 89-528 of SEQ ID NO: 2, the variant comprising a deletion at P229 of the native β-hexosaminidase α subunit sequence (SEQ ID NO: 1), wherein the variant β-hexosaminidase α subunit forms a homodimer.

\* \* \* \* \*

SEQUENCE LISTING

```
<160> NUMBER OF SEQ ID NOS: 4

<210> SEQ ID NO 1
<211> LENGTH: 529
<212> TYPE: PRT
<213> ORGANISM: Homo sapiens
<220> FEATURE:
<221> NAME/KEY: SIGNAL
<222> LOCATION: (1)..(22)
<220> FEATURE:
<221> NAME/KEY: PROPEP
<222> LOCATION: (23)..(88)
<220> FEATURE:
<221> NAME/KEY: CHAIN
<222> LOCATION: (89)..(529)

<400> SEQUENCE: 1

Met Thr Ser Ser Arg Leu Trp Phe Ser Leu Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
        35                  40                  45

Asp Val Ser Ser Ala Ala Gln Pro Gly Cys Ser Val Leu Asp Glu Ala
    50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
        115                 120                 125

Ser Glu Thr Val Trp Gly Ala Leu Arg Gly Leu Glu Thr Phe Ser Gln
    130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175
```

-continued

```
Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
        195                 200                 205

Pro Ser Phe Pro Tyr Glu Ser Phe Thr Phe Pro Glu Leu Met Arg Lys
    210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
        275                 280                 285

Pro Val Asn Pro Ser Leu Asn Asn Thr Tyr Glu Phe Met Ser Thr Phe
    290                 295                 300

Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
            340                 345                 350

Ser Phe Tyr Ile Gln Thr Leu Leu Asp Ile Val Ser Ser Tyr Gly Lys
        355                 360                 365

Gly Tyr Val Val Trp Gln Glu Val Phe Asp Asn Lys Val Lys Ile Gln
    370                 375                 380

Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
            420                 425                 430

Asp Phe Tyr Ile Val Glu Pro Leu Ala Phe Glu Gly Thr Pro Glu Gln
        435                 440                 445

Lys Ala Leu Val Ile Gly Gly Glu Ala Cys Met Trp Gly Glu Tyr Val
    450                 455                 460

Asp Asn Thr Asn Leu Val Pro Arg Leu Trp Pro Arg Ala Gly Ala Val
465                 470                 475                 480

Ala Glu Arg Leu Trp Ser Asn Lys Leu Thr Ser Asp Leu Thr Phe Ala
                485                 490                 495

Tyr Glu Arg Leu Ser His Phe Arg Cys Glu Leu Leu Arg Arg Gly Val
            500                 505                 510

Gln Ala Gln Pro Leu Asn Val Gly Phe Cys Glu Gln Glu Phe Glu Gln
        515                 520                 525

Thr

<210> SEQ ID NO 2
<211> LENGTH: 528
<212> TYPE: PRT
<213> ORGANISM: Artificial Sequence
<220> FEATURE:
<223> OTHER INFORMATION: Mutated Beta Hexosaminidase A subunit
      comprising mutations at S184, P209, N228, P229, V230, T231, P429,
      K432, D433, I436, N466, S491, L493, T494, F495, E498, L508, Q513,
      N518, V519, F521, E523 with reference to the wild-type sequence
      for the alpha subunit.
```

```
<220> FEATURE:
<221> NAME/KEY: SIGNAL
<222> LOCATION: (1)..(22)
<220> FEATURE:
<221> NAME/KEY: PROPEP
<222> LOCATION: (23)..(88)
<220> FEATURE:
<221> NAME/KEY: CHAIN
<222> LOCATION: (89)..(528)

<400> SEQUENCE: 2

Met Thr Ser Ser Arg Leu Trp Phe Ser Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
            35                  40                  45

Asp Val Ser Ser Ala Ala Gln Pro Gly Cys Ser Val Leu Asp Glu Ala
            50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
                100                 105                 110

Val Glu Asn Tyr Thr Leu Thr Ile Asn Asp Asp Gln Cys Leu Leu Leu
                115                 120                 125

Ser Glu Thr Val Trp Gly Ala Leu Arg Gly Leu Glu Thr Phe Ser Gln
130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Lys Ser Ile Leu Asp Thr Leu Asp Val
                180                 185                 190

Met Ala Tyr Asn Lys Leu Asn Val Phe His Trp His Leu Val Asp Asp
                195                 200                 205

Gln Ser Phe Pro Tyr Glu Ser Phe Thr Phe Pro Glu Leu Met Arg Lys
                210                 215                 220

Gly Ser Tyr Ser Leu Ser His Ile Tyr Thr Ala Gln Asp Val Lys Glu
225                 230                 235                 240

Val Ile Glu Tyr Ala Arg Leu Arg Gly Ile Arg Val Leu Ala Glu Phe
                245                 250                 255

Asp Thr Pro Gly His Thr Leu Ser Trp Gly Pro Gly Ile Pro Gly Leu
                260                 265                 270

Leu Thr Pro Cys Tyr Ser Gly Ser Glu Pro Ser Gly Thr Phe Gly Pro
                275                 280                 285

Val Asn Pro Ser Leu Asn Asn Thr Tyr Glu Phe Met Ser Thr Phe Phe
                290                 295                 300

Leu Glu Val Ser Ser Val Phe Pro Asp Phe Tyr Leu His Leu Gly Gly
305                 310                 315                 320

Asp Glu Val Asp Phe Thr Cys Trp Lys Ser Asn Pro Glu Ile Gln Asp
                325                 330                 335

Phe Met Arg Lys Lys Gly Phe Gly Glu Asp Phe Lys Gln Leu Glu Ser
                340                 345                 350

Phe Tyr Ile Gln Thr Leu Leu Asp Ile Val Ser Ser Tyr Gly Lys Gly
```

```
                  355                 360                 365
Tyr Val Val Trp Gln Glu Val Phe Asp Asn Lys Val Lys Ile Gln Pro
    370                 375                 380

Asp Thr Ile Ile Gln Val Trp Arg Glu Asp Ile Pro Val Asn Tyr Met
385                 390                 395                 400

Lys Glu Leu Glu Leu Val Thr Lys Ala Gly Phe Arg Ala Leu Leu Ser
                405                 410                 415

Ala Pro Trp Tyr Leu Asn Arg Ile Ser Tyr Gly Gln Asp Trp Arg Lys
            420                 425                 430

Phe Tyr Lys Val Glu Pro Leu Ala Phe Glu Gly Thr Pro Glu Gln Lys
        435                 440                 445

Ala Leu Val Ile Gly Gly Glu Ala Cys Met Trp Gly Glu Tyr Val Asp
    450                 455                 460

Ala Thr Asn Leu Val Pro Arg Leu Trp Pro Arg Ala Gly Ala Val Ala
465                 470                 475                 480

Glu Arg Leu Trp Ser Asn Lys Leu Thr Arg Asp Met Asp Asp Ala Tyr
                485                 490                 495

Asp Arg Leu Ser His Phe Arg Cys Glu Leu Val Arg Arg Gly Val Ala
            500                 505                 510

Ala Gln Pro Leu Tyr Ala Gly Tyr Cys Asn Gln Glu Phe Glu Gln Thr
        515                 520                 525

<210> SEQ ID NO 3
<211> LENGTH: 1584
<212> TYPE: DNA
<213> ORGANISM: Artificial Sequence
<220> FEATURE:
<223> OTHER INFORMATION: Artificial sequence coding for the mutant Beta
      Hexosaminidase A subunit of SEQ ID NO: 2.

<400> SEQUENCE: 3
atgacctctt ctagactgtg gttcagcctg ctgctcgccg cagcctttgc cggacgggcc      60
accgctcttt ggccgtggcc ccagaacttc agacctctg accagcggta cgtgctttac     120
ccaaataact tccagtttca gtacgatgtg tccagcgccg ctcagccggg ctgttccgtg     180
ctggacgagg ccttccaacg ctatcgcgac cttcttttcg gatctggctc ctggccaagg     240
ccatatctca ccggaaagag acacaccctt gagaagaacg tcctcgtggt gagcgtggtg     300
accccctggt gtaatcaact gccgaccctg aatctgtcg agaattacac tctgactatt      360
aacgacgacc aatgcctgct tctgtctgaa actgtctggg gagcactgcg gggacttgaa     420
accttcagcc agctggtgtg gaagtcagca gagggaacct tcttcatcaa taagaccgaa     480
atcgaggatt tccccgcctt ccctcatcgg ggactgctgc tggacactag ccgccattat     540
cttccgctta gtccattct ggataccctc gacgtgatgg catacaacaa actcaatgtg      600
ttccactggc atctggtgga cgaccagtca tttccctacg agtccttcac cttccccgaa     660
ctcatgagga agggaagcta ctctctcagc cacatctaca ccgcccaaga cgtcaaggaa     720
gtcatcgaat atgcacgcct gcgcggaatt agagtgctcg ccgagttcga caccccatggg    780 cacacccctga ctgggggacc tggcatccct ggtctgctca ctccctgcta ttcagggtca    840
gaaccttccg tactttgg ccctgtcaat cctagcctga acaatactta cgagtttatg       900
tctactttct tccttgaagt ctcatcagtc tttccagact tctatctgca tctcggaggt     960
gatgaagtgg acttcacctg ttggaagtca accccgaaa ttcaagactt tatgcggaag     1020
aagggtttcg gagaggattt caaacaactg gagagcttct acatccagac ccttctcgac    1080
```

-continued

```
atcgtgtcct catacgggaa aggttacgtg gtctggcagg aagtgttcga caataaggtg    1140
aagattcagc ccgacaccat tatccaagtc tggcgggagg acatcccagt gaactacatg    1200
aaggaacttg agctggtgac taaggctggg ttccgcgctc ttctcagcgc tccatggtat    1260
ctcaatcgga tctcttacgg acaggattgg aggaagttct acaaagtcga acccctggct    1320
ttcgagggga cccctgagca gaaggctctt gtgatcggag gcgaggcctg catgtgggga    1380
gagtacgtgg atgccaccaa cctggtgccc agactttggc caagggccgg tgccgtggct    1440
gaacgcctgt ggtcaaataa gctgacccgc gatatggacg acgcctatga tagactttca    1500
catttccggt gcgaactggt gcggagaggg gtggctgccc agccgctgta cgccgggtac    1560
tgcaaccagg agtttgagca gact                                           1584
```

<210> SEQ ID NO 4
<211> LENGTH: 556
<212> TYPE: PRT
<213> ORGANISM: Homo sapiens
<220> FEATURE:
<221> NAME/KEY: SIGNAL
<222> LOCATION: (1)..(42)
<220> FEATURE:
<221> NAME/KEY: PROPEP
<222> LOCATION: (43)..(121)
<220> FEATURE:
<221> NAME/KEY: CHAIN
<222> LOCATION: (122)..(556)

<400> SEQUENCE: 4

```
Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
                20                  25                  30

Val Ala Leu Val Val Gln Val Ala Glu Ala Ala Arg Ala Pro Ser Val
            35                  40                  45

Ser Ala Lys Pro Gly Pro Ala Leu Trp Pro Leu Pro Leu Ser Val Lys
        50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
                85                  90                  95

Ala Phe Arg Arg Tyr His Gly Tyr Ile Phe Gly Phe Tyr Lys Trp His
                100                 105                 110

His Glu Pro Ala Glu Phe Gln Ala Lys Thr Gln Val Gln Gln Leu Leu
            115                 120                 125

Val Ser Ile Thr Leu Gln Ser Glu Cys Asp Ala Phe Pro Asn Ile Ser
        130                 135                 140

Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
                180                 185                 190

Thr Ile Ile Asp Ser Pro Arg Phe Ser His Arg Gly Ile Leu Ile Asp
            195                 200                 205

Thr Ser Arg His Tyr Leu Pro Val Lys Ile Ile Leu Lys Thr Leu Asp
        210                 215                 220

Ala Met Ala Phe Asn Lys Phe Asn Val Leu His Trp His Ile Val Asp
225                 230                 235                 240
```

-continued

```
Asp Gln Ser Phe Pro Tyr Gln Ser Ile Thr Phe Pro Glu Leu Ser Asn
                245                 250                 255

Lys Gly Ser Tyr Ser Leu Ser His Val Tyr Thr Pro Asn Asp Val Arg
            260                 265                 270

Met Val Ile Glu Tyr Ala Arg Leu Arg Gly Ile Arg Val Leu Pro Glu
        275                 280                 285

Phe Asp Thr Pro Gly His Thr Leu Ser Trp Gly Lys Gly Gln Lys Asp
    290                 295                 300

Leu Leu Thr Pro Cys Tyr Ser Arg Gln Asn Lys Leu Asp Ser Phe Gly
305                 310                 315                 320

Pro Ile Asn Pro Thr Leu Asn Thr Thr Tyr Ser Phe Leu Thr Thr Phe
                325                 330                 335

Phe Lys Glu Ile Ser Glu Val Phe Pro Asp Gln Phe Ile His Leu Gly
            340                 345                 350

Gly Asp Glu Val Glu Phe Lys Cys Trp Glu Ser Asn Pro Lys Ile Gln
        355                 360                 365

Asp Phe Met Arg Gln Lys Gly Phe Gly Thr Asp Phe Lys Lys Leu Glu
    370                 375                 380

Ser Phe Tyr Ile Gln Lys Val Leu Asp Ile Ile Ala Thr Ile Asn Lys
385                 390                 395                 400

Gly Ser Ile Val Trp Gln Glu Val Phe Asp Asp Lys Ala Lys Leu Ala
                405                 410                 415

Pro Gly Thr Ile Val Glu Val Trp Lys Asp Ser Ala Tyr Pro Glu Glu
            420                 425                 430

Leu Ser Arg Val Thr Ala Ser Gly Phe Pro Val Ile Leu Ser Ala Pro
        435                 440                 445

Trp Tyr Leu Asp Leu Ile Ser Tyr Gly Gln Asp Trp Arg Lys Tyr Tyr
    450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                485                 490                 495

Asn Leu Thr Pro Arg Leu Trp Pro Arg Ala Ser Ala Val Gly Glu Arg
            500                 505                 510

Leu Trp Ser Ser Lys Asp Val Arg Asp Met Asp Asp Ala Tyr Asp Arg
        515                 520                 525

Leu Thr Arg His Arg Cys Arg Met Val Glu Arg Gly Ile Ala Ala Gln
    530                 535                 540

Pro Leu Tyr Ala Gly Tyr Cys Asn His Glu Asn Met
545                 550                 555
```